(12) United States Patent
Gellman et al.

(10) Patent No.: US 8,764,622 B2
(45) Date of Patent: Jul. 1, 2014

(54) MEDICAL SLINGS

(75) Inventors: Barry N. Gellman, North Easton, MA (US); Art Madenjian, Winchester, MA (US); Doreen Rao, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 67 days.

(21) Appl. No.: 13/177,830

(22) Filed: Jul. 7, 2011

(65) Prior Publication Data
US 2011/0263927 A1 Oct. 27, 2011

Related U.S. Application Data

(60) Continuation of application No. 11/429,121, filed on May 5, 2006, now Pat. No. 7,981,022, which is a division of application No. 10/460,112, filed on Jun. 12, 2003, now Pat. No. 7,070,558, which is a continuation-in-part of application No. 09/916,983, filed on Jul. 27, 2001, now Pat. No. 6,755,781.

(60) Provisional application No. 60/388,109, filed on Jun. 12, 2002.

(51) Int. Cl.
*A61F 2/02* (2006.01)

(52) U.S. Cl.
USPC .......................................................... 600/30

(58) Field of Classification Search
CPC ... A61F 2/0036; A61F 2/0045; A61F 2/0095; A61F 2/0004; A61F 2210/0004; A61F 2250/0097
USPC .......... 600/29–32, 37; 128/897, 898, DIG. 25
See application file for complete search history.

(56) References Cited

U.S. PATENT DOCUMENTS

| | | | |
|---|---|---|---|
| 2,687,723 A | 8/1952 | Stern | |
| 2,671,444 A | 3/1954 | Pease, Jr. | |
| 3,054,406 A | 9/1962 | Usher | |
| 3,124,136 A | 3/1964 | Usher | |
| 3,364,200 A | 1/1968 | Ashton | |
| 3,441,021 A | 4/1969 | Vickery | |
| 3,580,313 A | 5/1971 | mcKnight | |
| 3,666,750 A | 5/1972 | Briskin et al. | |
| 3,705,575 A | 12/1972 | Edwards | |
| 3,744,495 A | 7/1973 | Johnson | |

(Continued)

FOREIGN PATENT DOCUMENTS

| | | |
|---|---|---|
| DE | 19544162 | 4/1997 |
| EP | 0248544 | 4/1991 |

(Continued)

OTHER PUBLICATIONS

Araki, "The Loop-Loosening Procedure for Urination Difficulties After Stamey Spension of the Vesical Neck," Journal of Urology, 144:319-323, (1990).
Bayer, "A new approach to primary strengthening of colostomy with Marlex® Mesh to prevent paracolostomy hernia," Surgery, Gynecology and Obstetrics, 163:579-580, (1986).
Beck, "A 25-Year Experience with 519 Anterior Colporrhaphy Procedures," Obstetrics and Gynecology, 78:1011-1018, (1991).
Benderev, "A Modified Percutaneo Outpatient Bladder Neck Spension System," Journal of Urology, 152:2316-2320, (1994).

(Continued)

*Primary Examiner* — Samuel Gilbert

(57) ABSTRACT

A sling in accordance with the invention includes a synthetic material and a non-synthetic material positioned adjacent thereto. The non-synthetic material may be wrapped around or may be attached to the synthetic material. Additionally, the non-synthetic material may include slits. Methods for making such slings are also described.

19 Claims, 16 Drawing Sheets

(56) References Cited

U.S. PATENT DOCUMENTS

| | | |
|---|---|---|
| 4,085,756 A | 4/1978 | Weaver |
| 4,172,458 A | 10/1979 | Pereyra |
| 4,193,137 A | 3/1980 | Heck |
| 4,347,847 A | 9/1982 | Usher |
| 4,400,833 A | 8/1983 | Kurland |
| 4,409,974 A | 10/1983 | Freeland |
| 4,414,967 A | 11/1983 | Shapiro |
| 4,452,245 A | 6/1984 | Usher |
| 4,520,821 A | 6/1985 | Schmidt et al. |
| 4,545,374 A | 10/1985 | Jacobson |
| 4,549,545 A | 10/1985 | Levy |
| 4,584,722 A | 4/1986 | Levy et al. |
| 4,585,458 A | 4/1986 | Kurland |
| 4,633,873 A | 1/1987 | Dumican et al. |
| 4,652,264 A | 3/1987 | Dumican |
| 4,655,221 A | 4/1987 | Devereux |
| 4,741,330 A | 5/1988 | Hayhurst |
| 4,769,038 A | 9/1988 | Bendavid et al. |
| 4,784,126 A | 11/1988 | Hourahane |
| 4,801,299 A | 1/1989 | Brendel et al. |
| 4,838,884 A | 6/1989 | Dumican et al. |
| 4,854,316 A | 8/1989 | Davis |
| 4,857,041 A | 8/1989 | Annis et al. |
| 4,872,451 A | 10/1989 | Moore et al. |
| 4,873,977 A | 10/1989 | Ayant et al. |
| 4,905,692 A | 3/1990 | More |
| 4,911,165 A | 3/1990 | Lennard et al. |
| 4,938,760 A | 7/1990 | Burton et al. |
| 4,969,892 A | 11/1990 | Burton et al. |
| 4,973,300 A | 11/1990 | Wright |
| 4,986,831 A | 1/1991 | King et al. |
| 4,997,434 A | 3/1991 | Seedhom et al. |
| 5,002,551 A | 3/1991 | Linsky et al. |
| 5,012,822 A | 5/1991 | Schwarz |
| 5,013,292 A | 5/1991 | Lemay |
| 5,019,032 A | 5/1991 | Robertson |
| 5,026,398 A | 6/1991 | May et al. |
| 5,064,434 A | 11/1991 | Haber |
| 5,112,344 A | 5/1992 | Petros |
| 5,122,155 A | 6/1992 | Eberbach |
| 5,147,374 A | 9/1992 | Fernandez |
| 5,149,329 A | 9/1992 | Richardson |
| 5,176,692 A | 1/1993 | Wilk et al. |
| 5,178,630 A | 1/1993 | Schmitt |
| 5,195,542 A | 3/1993 | Gazielly et al. |
| 5,252,701 A | 10/1993 | Jarrett et al. |
| 5,254,133 A | 10/1993 | Seid |
| 5,256,133 A | 10/1993 | Spitz |
| 5,258,000 A | 11/1993 | Gianturco |
| 5,263,969 A | 11/1993 | Phillips |
| 5,289,963 A | 3/1994 | McGarry et al. |
| 5,290,217 A | 3/1994 | Campos |
| 5,292,328 A | 3/1994 | Hain et al. |
| 5,304,220 A | 4/1994 | Maginot |
| 5,328,077 A | 7/1994 | Lou |
| 5,337,736 A | 8/1994 | Reddy |
| 5,354,292 A | 10/1994 | Braeuer et al. |
| 5,356,064 A | 10/1994 | Green et al. |
| 5,362,294 A | 11/1994 | Seitzinger |
| 5,364,002 A | 11/1994 | Green et al. |
| 5,366,460 A | 11/1994 | Eberbach |
| 5,366,479 A | 11/1994 | McGarry et al. |
| 5,368,602 A | 11/1994 | de la Torre |
| 5,370,650 A | 12/1994 | Tovey et al. |
| 5,381,943 A | 1/1995 | Allen et al. |
| 5,383,477 A | 1/1995 | DeMatteis |
| 5,397,332 A | 3/1995 | Kammerer et al. |
| 5,425,737 A | 6/1995 | Burbank et al. |
| 5,425,984 A | 6/1995 | Kennedy et al. |
| 5,437,603 A | 8/1995 | Cerny et al. |
| 5,441,508 A | 8/1995 | Gazielly et al. |
| 5,451,235 A | 9/1995 | Lock |
| 5,474,543 A | 12/1995 | McKay et al. |
| 5,507,796 A | 4/1996 | Hasson |
| 5,527,341 A | 6/1996 | Gogolewski et al. |
| 5,527,342 A | 6/1996 | Pietrzak et al. |
| 5,544,664 A | 8/1996 | Benderev et al. |
| 5,549,619 A | 8/1996 | Peters et al. |
| 5,569,273 A | 10/1996 | Titone et al. |
| 5,582,188 A | 12/1996 | Benderev et al. |
| 5,591,163 A | 1/1997 | Thompson |
| 5,611,515 A | 3/1997 | Benderev et al. |
| 5,620,012 A | 4/1997 | Benderev et al. |
| 5,634,931 A | 6/1997 | Kugel |
| 5,634,944 A | 6/1997 | Magram |
| 5,635,379 A | 6/1997 | Deghenghi |
| 5,641,502 A | 6/1997 | Skalla et al. |
| 5,641,566 A | 6/1997 | Kranzler et al. |
| 5,643,288 A | 7/1997 | Thompson |
| 5,643,596 A | 7/1997 | Pruss et al. |
| 5,645,849 A | 7/1997 | Pruss et al. |
| 5,645,915 A | 7/1997 | Kranzler et al. |
| 5,681,310 A | 10/1997 | Yuan et al. |
| 5,690,655 A | 11/1997 | Hart et al. |
| 5,697,931 A | 12/1997 | Thompson |
| 5,707,647 A | 1/1998 | Dunn et al. |
| 5,733,337 A | 3/1998 | Carr, Jr. et al. |
| 5,766,221 A | 6/1998 | Benderev et al. |
| 5,769,864 A | 6/1998 | Kugel |
| 5,807,403 A | 9/1998 | Bevar et al. |
| 5,813,975 A | 9/1998 | Valenti |
| 5,816,258 A | 10/1998 | Jervis |
| 5,824,082 A | 10/1998 | Brown |
| 5,836,314 A | 11/1998 | Benderev et al. |
| 5,836,961 A | 11/1998 | Kieturakis et al. |
| 5,840,011 A | 11/1998 | Landgrebe et al. |
| 5,899,909 A | 5/1999 | Claren et al. |
| 5,916,225 A | 6/1999 | Kugel |
| 5,922,026 A | 7/1999 | Chin |
| 5,934,283 A | 8/1999 | Willem et al. |
| 5,997,554 A | 12/1999 | Thompson |
| 6,039,686 A | 3/2000 | Kovac |
| 6,042,534 A * | 3/2000 | Gellman et al. ............... 600/30 |
| 6,042,536 A | 3/2000 | Tihon et al. |
| 6,042,583 A | 3/2000 | Thompson et al. |
| 6,053,935 A | 4/2000 | Brenneman et al. |
| 6,059,801 A | 5/2000 | Samimi |
| 6,068,591 A | 5/2000 | Bruckner et al. |
| 6,074,419 A | 6/2000 | Healy et al. |
| 6,090,116 A | 7/2000 | D'Aversa et al. |
| 6,099,547 A | 8/2000 | Gellman et al. |
| 6,102,921 A | 8/2000 | Zhu et al. |
| 6,110,101 A | 8/2000 | Tihon et al. |
| 6,221,005 B1 | 4/2001 | Bruckner et al. |
| 6,273,852 B1 | 8/2001 | Lehe et al. |
| 6,306,079 B1 | 10/2001 | Trabucco |
| 6,319,264 B1 | 11/2001 | Tormala et al. |
| 6,368,859 B1 | 4/2002 | Atala |
| 6,685,626 B2 | 2/2004 | Wironen |
| 6,736,823 B2 | 5/2004 | Darois et al. |
| 6,911,003 B2 * | 6/2005 | Anderson et al. .............. 600/30 |
| 2002/0095064 A1 | 7/2002 | Beyar |
| 2005/0043820 A1 * | 2/2005 | Browning ................. 623/23.74 |
| 2005/0155608 A1 | 7/2005 | Pavcnik et al. |

FOREIGN PATENT DOCUMENTS

| | | |
|---|---|---|
| EP | 0599772 | 2/1997 |
| EP | 0334046 | 6/1997 |
| EP | 0677297 | 12/2000 |
| EP | 0778749 | 12/2000 |
| GB | 2268690 | 1/1994 |
| JP | 6114067 | 4/1994 |
| SE | 503271 | 4/1996 |
| SE | 506164 | 11/1997 |
| WO | WO-88/01853 | 3/1988 |
| WO | WO-92/16152 | 10/1992 |
| WO | WO-93/10715 | 6/1993 |
| WO | WO-93/10731 | 6/1993 |
| WO | WO-93/19678 | 10/1993 |
| WO | WO-94/19029 | 9/1994 |
| WO | WO-94/28799 | 12/1994 |
| WO | WO-96/06567 | 3/1996 |
| WO | WO-97/13465 | 4/1997 |

(56) References Cited

FOREIGN PATENT DOCUMENTS

| WO | WO-97/30638 | 8/1997 |
| WO | WO-97/43982 | 11/1997 |
| WO | WO-98/12971 | 4/1998 |
| WO | WO 98/35632 | 8/1998 |
| WO | WO-98/35632 | 8/1998 |
| WO | WO-99/16381 | 4/1999 |
| WO | WO-00/74633 | 12/2000 |
| WO | WO-01/39670 | 6/2001 |
| WO | 02/19945 | 3/2002 |
| WO | WO 03/007847 | 1/2003 |
| WO | WO 2004/043294 | 5/2004 |

OTHER PUBLICATIONS

Benderev, "A New Endoscopic Bladder Neck Spension for the Outpatient Treatment of Stress Urinary Incontinence," (video v-40), Journal of Urology, 149:197A, (1993).

Benderev, "Anchor Fixation and Other Modifications of Endoscopic Bladder Neck Spension," Journal of Urology, 40:409-418, (1992).

Blaivas et al., "Pubovaginal Fascial Sling for the Treatment of Complicated Stress Urinary Incontinence," Journal of Urology, 145:1214-1218, (1991).

Blaivas et al., "Successful Pubovaginal Sling Surgery," Contemporary Urology, pp. 40-63, (1993).

Cruikshank et al., "Anterior Vaginal Wall Culdeplasty at Vaginal Hysterectomy to Prevent Posthysterectomy Anterior Vaginal Wall Prolapse," American Journal of Obstretrics and Gynecology, 174:1863-1872, (1996).

Cruikshank, "Reconstructive Procedures for the Gynecologic Surgeon," American Journal of Obstetrics and Gynecology, 168:469-475, (1993).

Delancey, "Structural Support of the urethra as it Relates to Stress Urinary Incontinence: The Hammock Hypothesis," American Journal of Obstetrics and Gynecology, 170:1713-1723, (1994).

Falconer, "Clinical Outcome and Changes in Connective Tissue metabolism After Intravaginal Slingplasty in Stress Incontinent Women," Int. Urogynecol., 7:133-137, (1996).

Forneret, "Cost-Effective Treatment of Female Stress Urinary Incontinence: Modified Pereyra Bladder Neck Spension," Urology, 25:365-367, (1985).

Gittes, "No-Incision Pubovaginal Spension for Stress Incontinence," Journal of Urology, 138:568-570, (1987).

Hancock, "Transpublic Spension of the Bladder Neck for Urinary Incontinence," Journal of Urology, 123:667-668, (1980).

Hoffman, "Transvestibular Retropublic Bladder Neck Spension: A Pilot Study," Journal of Reproductive Medicine, 40:181-184, (1995).

http://www.lifecell.com/about/science.cfm, (Jul. 24, 2001).

Iglesia et al., "The e of Mesh in Gynecologic Surgery," Journal of Int. Urogynecol., 8:105-115, (1997).

Kovac et al., "Pubic Bone Suburethral Stabilization Sling for Recurrent Urinary Incontinence," Obstetrics and Gynecology, 89:624-627, (1997).

Leach et al., "Modified Pereyra Bladder Neck Spension After Previously Failed anti-Incontinence Surgery: Surgical Technique and Results With Long-Term Follow-Up," Urology, 23:359-362. (1984).

Leach, "Bone Fixation Technique for Transvaginal Needle Spension," Urology, 31:388-390, (1988).

Mascio, "Therapy of urinary Stress Incontinence in Women: ing Mitek® GII Anchors," Mitek® Brochure, (1993).

Matapurkar et al., "A New Technique of "Marlex-peritoneal Sandwich" in the Repair of Large Incisional Hernias," World J. Surg., 15 (6):768-770, (1991).

Mattox et al., "Modification of the Miya Hook in Vaginal Colpopexy," The Journal of Reproductive Medicine, 40:681-683, (1995).

McKiel et al., "Marshall-Marchetti Procedure: Modification," Journal of Urology, 96:737-739, (1966).

Mitchell, "Hook Needle and Retractor for Posterior Urethroplasty," Journal of Urology, 42:599-600, (1970).

Nativ et al., "Bladder Neck Spension ing Bone Anchors for the Treatment of Female Stress Incontinence," ASAIO Journal, 204-208, (1997).

Nichols et al., "Identification of Pubourethral Ligaments and Their Role in Transvaginal Surgical Correction of Stress Incontinence," American J. Obstet. Gynecology, 115 (1), (1973).

Parra et al., "Experience With a Simplified Technique for the Treatment of Female Stress Urinary Incontinence," Urology, 66:617, (1990).

Pereyra et al., "A Simplified Surgical Procedure for the Correction of Stress Incontinence in Women," West J. Surg. Obstretrics and Gynecology, 223-226, (1959).

Petros, "Ambulatory Surgery for Urinary Incontinence and Vaginal Prolapse," Med. J. At., 161:171-172, (1994).

Petros, "The Intravaginal Slingplasty Operation, a Minimally Invasive Technique for Cure of Urinary Incontinence in the Female," At. NZ 1 Obsstet. Gynaecol, 36(4):453-461, (1996).

Raz, "Modified Bladder Neck Spension for Female Stress Incontinence," Urology, 17:82-85, (1981).

Richarson et al., "Treatment of Stress Urinary Incontinence Due to Paragainal Fascial Defect," Obstretics & Gynecology, 57(3), (1981).

Richmond et al., "Modification of the Bankart Reconstruction with a Suture Anchor: Report of a New Technique," Am. J. Sports Med., 19:343-346, (1991).

Schaeffer et al., "Endoscopic Spension of Vesical Neck for Urinary Incontinence," Urology, 23:484-494, (1984).

Schatzker et al., "The Rationale of Operative Fracture Care," Springer-Verlag, Berlin, p. 159, (1987).

Scheuer, "The Modified Pereyra Bladder Neck Spension Procedure: ing Mitek® GII Anchors," Mitek® Brochure, (1993).

Spencer et al., "A comparison of Endoscopic Spension of the Vesical Neck With Suprapublic Vesicourethropexy for Treatment of Stress Urinary Incontinence," Journal of Urology, 137:411-415. (1987).

Stamey et al., "Endoscopic Spension of the Vesical Neck for Urinary Incontinence in Females: Report on 203 Consecutive Patients," Ann. Surg., 192:465-471, (1980).

Stamey, "Endoscopic Spension of the Vesical Neck for Urinary Incontinence," Surgery, Gynecology and Obstretrics, 136:547-554, (1973).

Stamey, "Endoscopic Spension of the Vesical Neck," Surgery of Female Incontinence, 115, 132, (1986).

Trockman et al., "Modified Pereyra Bladder Neck Spension: 10-year mean follow-up ing outcomes analysis in 125 Patients," Journal of Urology, 154:1841-1847, (1995).

Ulmsten et al., "Treatment of Stress Urinary Incontinence Due to Paragainal Fascial Defect," Obstretics & Gynecology, 57(3), (1981).

Ulmsten et al., "An Ambulatory Surgical Procedure Under Local Anesthesia for Treatment of Female Urinary Incontinence," Journal of Int. Urogynecol., 7:81-86, (1996).

Vasavada et al., "Incisionless Pubovaginal Fascial Sling ing Transvaginal Bone Anchors for the Treatment of Stress Urinary Incontinence," Digital Urology Journal, http://www.duj.com/Article/Raz/Raz.html, (Jul. 24, 2001).

Webster et al., "Voiding Dysfunctional Following Cystourethropexy: Its Evaluation and Management," Journal of Urology, 144:670-673, (1990).

Webster, "Female Urinary Incontinence," Urologic Surgery, J.B. Lippincott Company: Philadelphia, 665-679, (1983).

Winter, "Peripubic Urethropexy for Urinary Stress Incontinence in Women," Urology, 20:408-411, (1982).

Zacharin, "Abdominoperineal Urethral Spension in the Management of Recurrent Stress Incontinence of Urine—a 15-year Experience," Obstetrics & Gynecology, 62(5):644-654, (1983).

Zimmern et al., "A Prospective Evaluation of Four-Corner Bladder Neck Spension for Grade II/III Cystocele Repair,". Neurol. and Urodynamics, 9:231, (1990).

Zimmern et al., "Transvaginal Closure of the Bladder Neck," Seminars in Urology, 4:30-32, (1986).

* cited by examiner

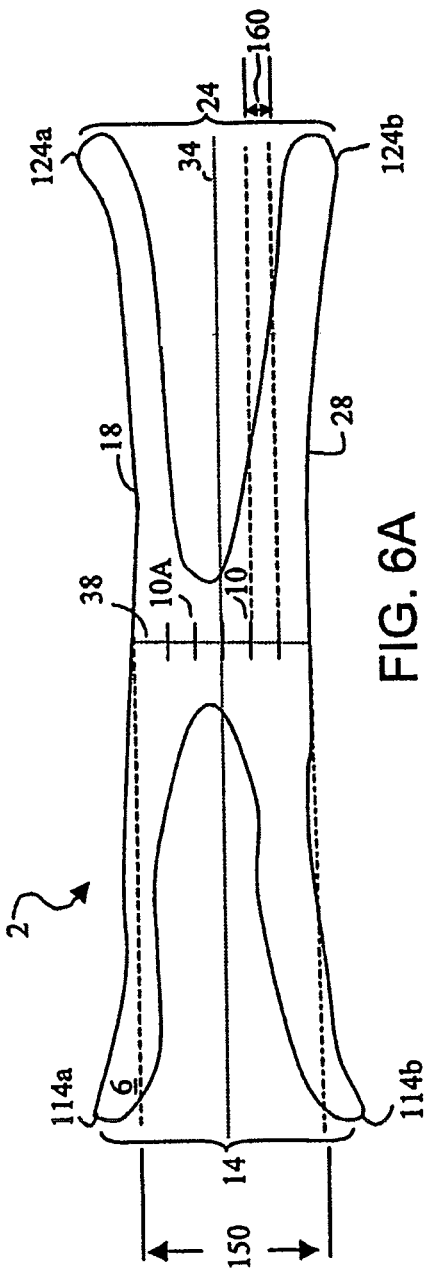
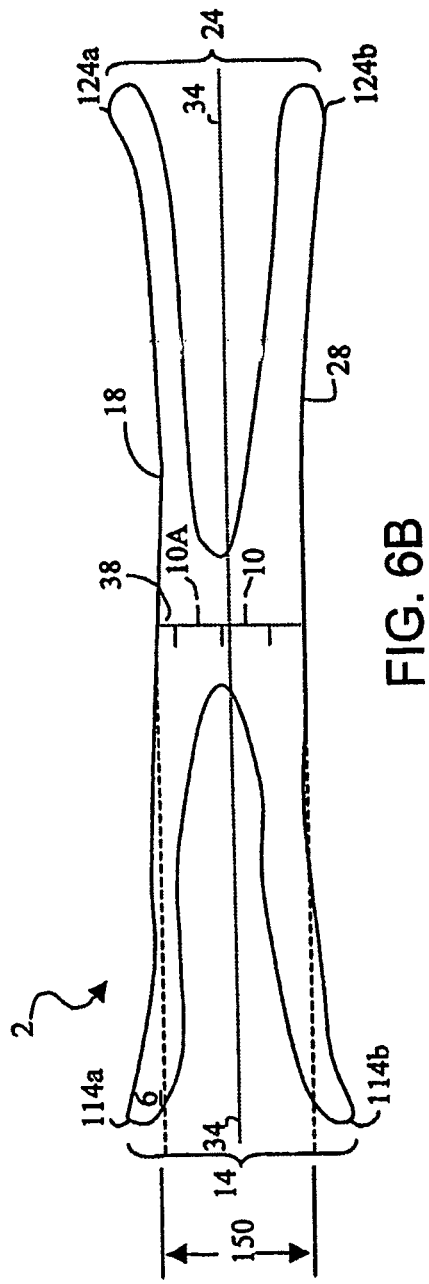

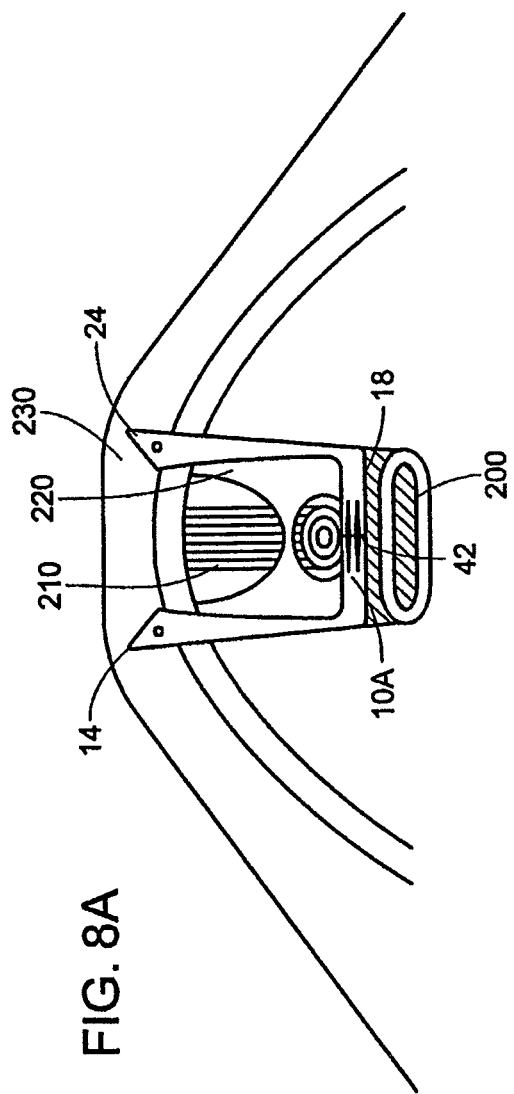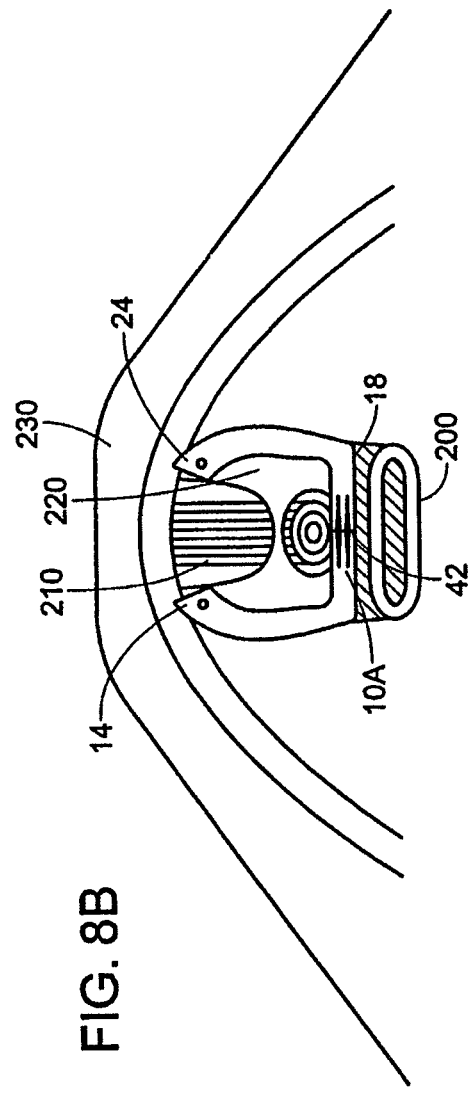

MEDICAL SLINGS

CROSS-REFERENCE TO RELATED APPLICATIONS

This application is a continuation of U.S. patent application Ser. No. 11/429,121, filed on May 5, 2006, which is a divisional of U.S. patent application Ser. No. 10/460,112, filed on Jun. 12, 2003, now U.S. Pat. No. 7,070,558, which is a continuation-in-part of U.S. patent application Ser. No. 09/916,983, filed on Jul. 27, 2001, now U.S. Pat. No. 6,755,781, and incorporates by reference, and claims priority to and the benefit of, provisional U.S. patent application Ser. No. 60/388,109, filed on Jun. 12, 2002.

TECHNICAL FIELD

This invention generally relates to medical slings, methods of making such slings, kits including such slings, and methods of treating a damaged portion of a patient's body using such slings.

BACKGROUND INFORMATION

Urinary incontinence is a disorder that generally affects people of all ages. The inability to control urination can impact a patient both physiologically and psychologically. Urinary incontinence can interfere with a patient's daily activity and impair quality of life. Stress urinary incontinence is one type of urinary incontinence. Actions including straining, coughing, and heavy lifting can cause those with stress urinary incontinence to void urine involuntarily.

Various physiological conditions cause urinary incontinence in women. Stress urinary incontinence generally is caused by two conditions that occur independently or in combination, intrinsic sphincter deficiency and hypermobility. Intrinsic sphincter deficiency (ISD) is a condition where the urethral sphincter fails to coapt properly. When functioning properly, the urethral sphincter muscles relax to enable the patient to void, and the sphincter muscles are otherwise constricted to retain urine. ISD may cause urine to leak out of the urethra during stressful actions. Hypermobility is a condition where the pelvic floor is weakened or damaged causing the bladder neck and proximal urethra to rotate and descend in response to increases in intraabdominal pressure. When intraabdominal pressure increases (due, for example, to strain resulting from coughing), the hypermobility condition may cause urine leakage. Some women suffer from a combination of ISD and hypermobility.

The methods for treating stress urinary incontinence include placing a sling to either compress the urethral sphincter or placing a sling to support, elevate or provide a "back stop" to the bladder neck and proximal urethra. Providing support to the bladder neck and proximal urethra maintains the urethra in the normal anatomical position and elevation places the urethra above the normal anatomical position. The "back stop" prevents descent according to the hammock theory such that the back stop prevents the bladder neck from descending upon application of strain.

Generally, slings are employed to support anatomical structures. Slings may be made from one or more materials derived from non-synthetic material(s), for example, mammalian tissue(s), synthetic material(s), or from a combination of non-synthetic material(s) and synthetic material(s).

The presence of non-synthetic material(s) can prevent erosion and irritation, caused by the use of synthetic materials alone. It has been observed that the interaction between the synthetic material of a sling and the body may cause erosion into the body, e.g., the urethra or vagina. The incorporation of non-synthetic material(s) into the sling prevents this erosion, thereby increasing patient comfort.

After implantation in a patient, slings made from mammalian tissues typically require a six to twelve month period to be absorbed by the patient's body, after which the implanted mammalian tissue is not recognizable from the patient's surrounding tissue. Mammalian tissue slings include tissue harvested from the patient or a donor. In some instances, the mammalian tissue may be human cadaveric tissue.

SUMMARY OF THE INVENTION

The present invention relates to slings, methods of making such slings, medical kits including such slings, and methods of treating a damaged portion of a patient's body using such slings. Various known surgical procedures employ slings to support anatomical structures. Exemplary surgical applications include the treatment of urinary incontinence, the repair of herniation, and orthopedics generally.

In accordance with one aspect of the invention, cuts are disposed through the sling material to provide open areas in the sling, which enable rapid tissue in-growth into the sling material while maintaining a high tensile strength. The cuts can be slits, holes, and/or apertures. The sling with the cuts according to the invention maintains a substantially constant width during and after implantation in a patient's body. The risk of pressure necrosis or erosion of the damaged portion of the patient's body caused by uneven sling pressure is reduced because the sling width remains substantially constant even when the sling is stretched longitudinally during the implantation procedure.

The benefits of such a sling, which can comprise synthetic material, mammalian tissue, or a combination of synthetic and mammalian tissue material with cuts disposed through the material, include rapid fibrosing of the sling, a shortened healing period, and little or no sling movement after implantation. In accordance with the invention, when a sling is employed to treat female urinary incontinence connective tissue resembling scar tissue will begin to infiltrate one or more open areas disposed in the sling (which is positioned underneath the patient's urethra). The formation of scar tissue generally adds bulk that compresses the urethra and provides the support to improve patient continence. The scar tissue that infiltrates the sling holds the sling at the site of implantation and inhibits or prevents its movement.

In general, in one aspect, the invention involves a sling for use in a medical application. The sling is made of a sheet of synthetic material, mammalian tissue, or a combination of mammalian tissue and synthetic material. The sheet has a longitudinal axis with a first end portion and a second end portion. The second end portion of the sheet is disposed opposite and away from the first end portion along a longitudinal axis. The sheet also includes a first side and a second side; the second side is disposed opposite and away from the first side by a distance and along a perpendicular axis. The perpendicular axis is perpendicular or substantially perpendicular to the first axis (i.e., for example a longitudinal axis). The perpendicular axis intersects the longitudinal axis at the midpoint or substantially the midpoint of the longitudinal axis. The sheet further includes one or more cuts disposed substantially along at least a portion of the second axis (i.e., for example a perpendicular axis). The cuts are disposed such that upon exposure to tensioning force applied to the sheet substantially along the longitudinal axis during the medical application, the distance along the perpendicular axis remains substantially constant.

Embodiments of this aspect of the invention can include the following features. The cuts disposed on the sling may be a slit disposed through the sheet of material. The slits may be disposed such that at least some of the slits open upon exposure to the tensioning force applied during the medical application. The open slits provide open areas on the sling, which permit tissue crosslinking and in-growth therein when implanted inside the body of a patient.

Alternatively, the cuts may comprise any aperture disposed through the sheet of the sling. Upon exposure to the tensioning force applied during the medical application, at least some, and generally all, of the apertures on the sling remain open. The apertures that remain open provide open areas on the sling. The open areas permit tissue crosslinking and in-growth into the cuts when the sling is implanted inside the body of a patient. The cuts may be disposed substantially along the perpendicular axis of the sling. In some embodiments the cuts may be equidistant from one another.

In other embodiments, a line may be disposed, as a visual indicator, substantially along at least a portion of the perpendicular axis of the sling. The line can be made by applying a surgical ink to the sling material.

The material of the sling may be derived from mammalian tissue source(s), synthetic material(s), or a combination of mammalian tissue(s) and synthetic material(s). The mammalian tissue source may be human, human cadaveric, or tissue-engineered human tissue. The mammalian tissue may alternatively be from an animal source. Suitable sources of animal tissues may include porcine, ovine, bovine, and equine tissue sources. The material may be an omnidirectional material, a material that has equivalent tensile strength from any direction, such as pericardium or dermis. Alternatively, the material of the sling may be an oriented material, a material that has a single direction where the tensile strength of the material is the highest. Oriented materials may include rectus fascia and/or facia lata.

The synthetic material may be a solid material, a weave, a braid, a mesh, or some other suitable construction. The synthetic material source may be nylon, polyethylene, polyester, polypropylene, fluoropolymers, copolymers thereof, and other suitable synthetic materials. The material may be a synthetic material that is absorbable by the patient's body. Suitable absorbable synthetic materials may include polyglycolic acid, polylactic acid, and other suitable absorbable synthetic materials. The synthetic material may be oriented and have a single direction where the tensile strength of the material is highest. Alternatively, the material may be omnidirectional such that any direction of the synthetic material may have equivalent tensile strength.

The cuts can be formed through a sheet made of oriented tissue material along the grain, i.e., along a single direction where the tensile strength of the material is the highest. By disposing the cuts along the grain of the oriented material, the strength of the sheet may be substantially maintained. Upon exposure to tensioning force applied to the sheet substantially along the longitudinal axis, the distance along the perpendicular axis of the oriented sheet remains substantially constant. Likewise, by forming cuts through and along the highest tensile strength direction of a sheet of synthetic sling material, the strength of the synthetic sheet may be substantially maintained.

In one embodiment, one or more fasteners are disposed on the sheet of sling material. The fasteners may be disposed in regions of the sheet where there are no cuts. The fasteners may be disposed, for example, at each of the first end portion and the second end portion of the sheet. Alternatively, or in addition, one or more eyelets may be disposed through both the first end portion and the second end portion of the sheet. In one particular embodiment, a fastener, for example a suture, is secured to a sling by threading it through an eyelet disposed through the sling.

The sling of the invention may be made of a sheet that is in a shape suitable for a medical application. Suitable shapes may include rectangular and substantially rectangular. The sling may be octagonal, hexagonal, trapezoidal, elliptical, or some other shape that is suitable to the slings intended placement location within the body. In some embodiments, the sheet has elongated members, which extend substantially from a central portion of the sheet. The elongated members may be anchored to an anatomical structure in the patient without use of a suture.

In general, in another aspect, the invention relates to a method of making a sling by forming one or more cuts in a sheet of material provided in a shape suitable for use in a medical application. The sheet provided may be derived from mammalian tissue(s), synthetic material(s), or a combination of mammalian tissue(s) and synthetic material(s). The sheet includes a first end portion and a second end portion. The second end portion of the sheet is disposed opposite and away from the first end portion along a longitudinal axis. The sheet also includes a first side and a second side. The second side is disposed opposite and away from the first side by a distance and along a perpendicular axis. The perpendicular axis is substantially perpendicular to the longitudinal axis. The perpendicular axis intersects the longitudinal axis at substantially the midpoint of the longitudinal axis. The one or more cuts are formed substantially along at least a portion of the perpendicular axis of the sheet. The cuts are formed in the sheet such that the distance along the perpendicular axis of the sheet remains substantially constant upon exposure to the tensioning force applied to the sheet substantially along the longitudinal axis during a medical application.

Embodiments of this other aspect of the invention can include the following features. The method of making the sling can further comprise forming a line substantially along at least a portion of the perpendicular axis of the sling. The line can be formed by applying surgical ink to the sling material. The line may be used as a visual indicator during a medical application.

The method of making the sling can further comprise disposing one or more fasteners at the first end portion of the sheet. One or more fasteners may also be disposed at the second end portion of the sheet. The fasteners may be disposed on regions of the first end portion and the second end portion of the sheet where cuts are not disposed through the material.

The method of making the sling can further comprise sterilizing the material and sterilizing the sling according to methods known in the art to make the sling suitable for use in various medical applications. The method of making the sling may include packaging the sling in a sterile holder. According to methods of the invention, the sling may be packaged under conditions that are dry and protective from ultra-violet light.

In general, in a further aspect, the invention involves a method of treating a damaged portion of a patient's body. A sling is provided and then used. The sling is made of a sheet of material that has cuts disposed through the sheet to provide open areas upon implantation inside the patient's body. The material of the sheet may be derived from mammalian tissue(s), synthetic material(s), or a combination of mammalian tissue(s) and synthetic material(s). The sheet includes a first end portion and disposed opposite and away from the first end portion along a longitudinal axis is a second end portion. The sheet also includes a first side and disposed opposite and away from the first side by a distance and along a perpendicular axis is a second side. The perpendicular axis is substantially perpendicular to and intersects the longitudinal axis at substantially the midpoint of the longitudinal axis. The sheet further includes one or more cuts disposed substantially along at least a portion of the perpendicular axis. The first end portion of the sling sheet is secured to a first anatomical structure in the body of the patient. Tensioning force is applied substantially along the longitudinal axis of the sheet. The second end portion of the sling is secured to a second anatomical structure in the body of the patient. The sling is secured inside the body of the patient such that its perpendicular axis lies substantially along a portion of the patient's body. The one or more cuts are disposed such that the distance along the perpendicular axis of the sheet remains substantially constant when the sling is secured. The secured sling supports a damaged portion of the patient's body.

The method of using the sling of the invention may further comprise securing the first end portion to an anatomical structure using a surgical fastener. Surgical fasteners employed to secure the sling may include a suture, a clip, a bone anchor, a staple, or other suitable fasteners.

The sling may be secured to an anatomical structure in the body of the patient. Suitable anatomical structures include: bone, fascia, ligament, or muscle. Alternatively, the sling may be secured in an anchorless manner, in which the structure of sling (i.e., tanged portions) provides resistance against movement of the sling in the tissue while tissue in growth occurs.

The method of using the sling can further comprise centering the sling at the damaged portion of a patient's body using a line disposed substantially along at least a portion of the perpendicular axis as a visual indicator. The line may provide a visual indication of where the one or more cuts are disposed on the sling and the line may be employed to help align the cuts with the damaged portion of the patient's body.

When the cuts are slits, at least some of the slits can be open when supporting the damaged portion of the patient's body. Alternatively, when the cuts are apertures, at least some of the apertures can remain open when supporting the damaged portion of the patient's body. The open cuts provide open areas on the sling that permit the patient's tissue to crosslink and grow into the open areas on the sling once the sling is secured inside the body of the patient. The scar tissue ingrowth both secures the sling inside the patient's body and provides support to the areas of the body into which the tissues grow.

The method may further comprise evenly distributing pressure on a damaged portion of a patient's body with the secured sling material. In one embodiment, the sling is employed to treat a female patient with urinary incontinence. The sling material may be implanted to evenly distribute pressure on a patient's urethra. The sling may be delivered and implanted to treat female urinary incontinence according to transvaginal, transabdominal, supra-pubic, pre-pubic, or transobturator approaches, or some combination of these procedures.

In one embodiment, the sling is employed to treat a patient suffering from ISD. The sling may be implanted such that the one or more cuts on the sling contact the underside of the patient's sphincter muscle, the first side of the sling contacts the under portion of the distal bladder neck and second side of the sling contacts the under portion of the urethra. The sling can be implanted such that the sling material evenly distributes pressure on a patient's sphincter muscle without applying pressure to the urethra or bladderneck. Alternatively, the method may be employed to treat a patient with bladderneck hypermobility and the cuts on the sling may be placed adjacent to the patient's mid urethra.

The patient's body can absorb the material of the sling after implantation of the sling in the body. The sling material absorbed by the patient's body may be made from mammalian tissue. Alternatively, synthetic absorbable sling material may be absorbed by the patient's body after implantation therein.

In another aspect, the invention relates to a sling for use in a medical application including a sheet including a synthetic material. The sheet includes a first end portion and a second end portion, the second end portion disposed opposite and away from the first end portion along a first axis and a first side and a second side, the second side disposed opposite and away from the first side by a distance and along a second axis that is substantially perpendicular to the first axis and that intersects the first axis at substantially the midpoint of the first axis. The sheet further includes a non-synthetic material wrapped around at least a portion of the sheet.

In yet another aspect, the invention relates to a sling for use in a medical application including a sheet including a synthetic material. The sheet includes a first end portion and a second end portion, the second end portion disposed opposite and away from the first end portion along a first axis and a first side and a second side, the second side disposed opposite and away from the first side by a distance and along a second axis that is substantially perpendicular to the first axis and that intersects the first axis at substantially the midpoint of the first axis. The sheet further includes a non-synthetic material attached to the sheet by at least one of glue, a suture, a staple, a rivet, an eyelet rivet, a fastener, a clip, and combinations thereof.

In still another aspect, the invention relates to a sling for use in a medical application including a sheet including a synthetic material. The sheet includes a first end portion and a second end portion, the second end portion disposed opposite and away from the first end portion along a first axis and a first side and a second side, the second side disposed opposite and away from the first side by a distance and along a second axis that is substantially perpendicular to the first axis and that intersects the first axis at substantially the midpoint of the first axis. The sheet further includes a non-synthetic material disposed adjacent to the sheet, wherein the non-synthetic material defines at least one or more slits disposed substantially along at least a portion of the second axis.

In various embodiments of the foregoing aspect, at least some of the slits open upon exposure to a tensioning force applied during the medical application. Furthermore, each of the slits may include an aperture. The apertures may remain open after exposure to the tensioning force applied during the medical application. In another embodiment, the slits are disposed from the first side to the second side of the sheet substantially along the second axis. The slits may be disposed equidistant from one another substantially along the second axis.

In one embodiment of the foregoing aspects of the invention, the non-synthetic material wraps around at least a portion of the sheet. The non-synthetic material can be wrapped completely about at least a portion of the sheet. The non-synthetic material may be free floating about the sheet. In another embodiment, the non-synthetic material is disposed adjacent to at least a portion of one of a top surface and a bottom surface of the sheet. In yet another embodiment, the non-synthetic material is disposed adjacent to at least a portion of both the top surface and the bottom surface of the sheet. In yet another embodiment, the non-synthetic material may be attached to the sheet by at least one of glue, a suture, a staple, a rivet, an eyelet rivet, a fastener, a clip, and combinations thereof.

In various embodiments of the foregoing aspects of the invention, the sling further includes a second non-synthetic material disposed adjacent to the sheet and opposite the first non-synthetic material. In another embodiment, the non-synthetic material permits tissue in-growth therein when the sling is implanted in a body of a patient. The synthetic material may include a material selected from the group consisting of nylon, polyethylene, polyester, polypropylene, fluoropolymers, and combinations thereof.

In one embodiment, the non-synthetic material is disposed adjacent to a urethra when placed within a body of a patient. Additionally, the non-synthetic material can extend to each side of an endopelvic fascia when placed within a body of a patient. In various embodiments, the non-synthetic material is about 4 cm to about 10 cm in length along the first axis of the sheet. Alternatively, the non-synthetic material is about 5 cm to about 9 cm in length along the first axis of the sheet. Alternatively, the non-synthetic material is about 7 cm in length along the first axis of the sheet.

In various embodiments, the non-synthetic material is selected from the group consisting of bovine, porcine, ovine, equine, human cadaveric, and tissue-engineered tissues. In one embodiment, the non-synthetic material includes an acellular matrix processed from human skin. The non-synthetic material may be capable of remodeling into a healthy layer of tissue.

In other embodiments of the foregoing aspects, at least a portion of at least one of the first side and the second side may be tanged. Furthermore, at least a portion of at least one of the first side and the second side may be non-tanged. In various embodiments, the sheet includes a propylene mesh. Furthermore, the sheet may include fibers selected from the group consisting of colored, radiopaque, and combinations thereof. Moreover, the sheet may be of a type selected from the group consisting of woven, knitted, felted, non-woven and combinations thereof. In addition, the sheet may have a substantially rectangular shape. In another embodiment the sheet includes a coating. The coating may include a pharmaceutical for delivery to a patient when the sling is implanted in a body of the patient.

In another embodiment, the sling further includes a second sheet including a synthetic material including a first end portion and a second end portion, the second end portion disposed opposite and away from the first end portion along a first axis of the second sheet and a first side and a second side, the second side disposed opposite and away from the first side by a distance and along a second axis of the second sheet that is substantially perpendicular to the first axis and that intersects the first axis of the second sheet at substantially the midpoint of the first axis of the second sheet. The non-synthetic material may be positioned between the first end of the first sheet and the second end of the second sheet. Furthermore, the non-synthetic material may be attached to the first sheet and the second sheet by at least one of glue, a suture, a staple, a rivet, an eyelet rivet, a fastener, a clip, and combinations thereof.

In another aspect, the invention relates to a method of making a sling, including providing a sheet suitable for a medical application, the sheet including a synthetic material and including a first end portion and a second end portion, the second end portion disposed opposite and away from the first end portion along a first axis, the sheet also including a first side and a second side, the second side disposed opposite and away from the first side by a distance and along a second axis that is substantially perpendicular to the first axis, and that intersects the first axis at substantially the midpoint of the first axis. The method further includes positioning a non-synthetic material adjacent to at least a portion of the sheet, wherein the non-synthetic material is wrapped around at least a portion of the sheet.

In another aspect, the invention relates to a method of making a sling, including providing a sheet suitable for a medical application, the sheet including a synthetic material and including a first end portion and a second end portion, the second end portion disposed opposite and away from the first end portion along a first axis, the sheet also including a first side and a second side, the second side disposed opposite and away from the first side by a distance and along a second axis that is substantially perpendicular to the first axis, and that intersects the first axis at substantially the midpoint of the first axis. The method further includes attaching a non-synthetic material to the sheet by at least one of glue, a suture, a staple, a rivet, an eyelet rivet, a fastener, a clip, and combinations thereof.

In yet another aspect, the invention relates to a method of making a sling, including providing a sheet suitable for a medical application, the sheet including a synthetic material and including a first end portion and a second end portion, the second end portion disposed opposite and away from the first end portion along a first axis, the sheet also including a first side and a second side, the second side disposed opposite and away from the first side by a distance and along a second axis that is substantially perpendicular to the first axis, and that intersects the first axis at substantially the midpoint of the first axis. The method further includes positioning a non-synthetic material adjacent to the sheet and disposing at least one or more slits in the non-synthetic material substantially along at least a portion of the second axis.

In any of the embodiments of the aspects of the invention above, the sling may be encased wholly or partly within a protective sleeve. The sling may be free-floating within the sleeve or fastened to the sleeve at one or more points. The sleeve may aid in easing implantation of the sling and may protect the sling during implantation. The sleeve may be removed according to various methods once the sling has been implanted.

These and other objects, along with advantages and features of the present invention, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention. In the following description, various embodiments of the present invention are described with reference to the following drawings, in which:

FIG. 6A illustrates a plan view of another embodiment of a sling including two pairs of elongated members extending from a central portion of the sling in accordance with the invention;

FIG. 6B illustrates a plan view of another embodiment of a sling including two pairs of elongated members extending from a central portion of the sling in accordance with the invention;

FIG. 8A is a cross section of the female pelvis illustrating the location of a sling similar to the sling of FIG. 4 relative to the urethra and the vagina and anchored to the pubic bone;

FIG. 8B is a cross section of the female pelvis illustrating the location of a sling similar to the sling of FIG. 4 relative to the urethra and the vagina and anchored to facial urethra supports.

DESCRIPTION

Figure 1:
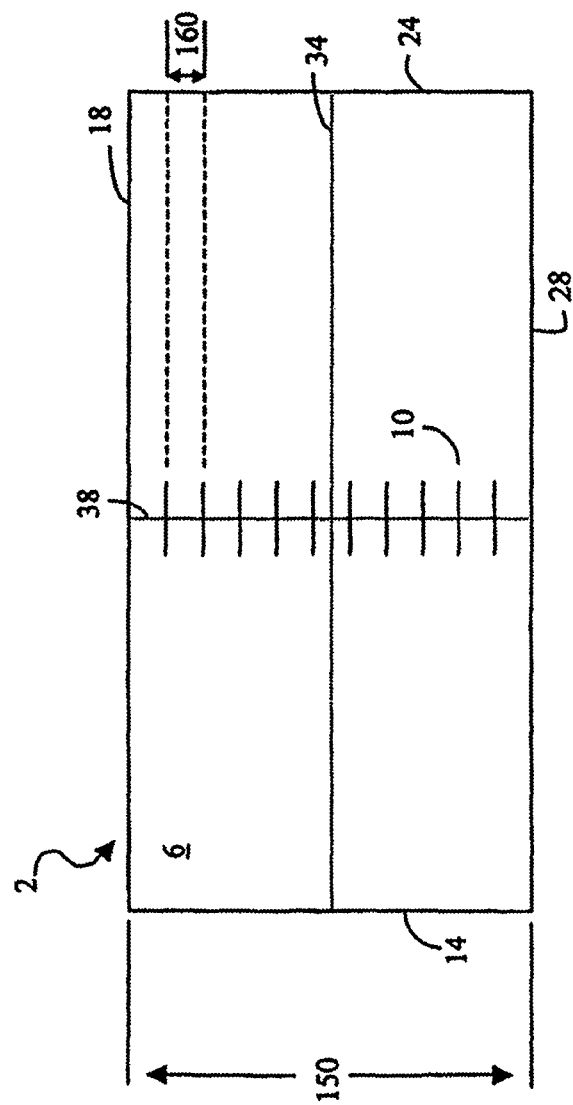
FIG. 1 illustrates a plan view of one embodiment of a sling according to the invention.

Referring to FIG. 1, in one embodiment according to the invention, a sling 2 is a substantially rectangular sheet 6 made of one or more materials. Sheet 6 includes a first end portion 14 at one end of the sheet 6 and a second end portion 24 at the opposite end of the sheet 6 along a first longitudinal axis 34. The sheet 6 also includes a first side 18 and a second side 28. The second side 28 is disposed opposite the first side 18 along a second axis 38 that is substantially perpendicular to the first longitudinal axis 34. The perpendicular axis 38 substantially bisects the longitudinal axis 34. The perpendicular axis 38 extends the distance 150 from the first side 18 to the second side 28.

Generally, the sizes and shapes of the mesh and the non-synthetic material comprising the sling will vary to suit a particular embodiment. The sling 2 can be rectangular or substantially rectangular in shape or the sling 2 can be an octagonal shape. In alternative embodiments, the sling 2 has other shapes suitable to its intended placement location within the body such as trapezoidal, hexagonal, or elliptical shapes. Exemplary shapes are described in U.S. Pat. No. 6,042,534, the disclosure of which is hereby incorporated by reference.

The sheet 6 includes one or more cuts 10 disposed along at least a portion of the length of the perpendicular axis 38. The cuts 10 are disposed such that the length of the perpendicular axis 38 remains substantially constant following the application of tension applied substantially along the longitudinal axis 34 of the sheet 6. Such tension may be applied, for example, during implantation of the sling 2 in a patient. The cuts 10 can be, for example, slits or alternatively apertures disposed through the full thickness of sheet 6. In some embodiments, the cuts 10 may not extend through the entire thickness of the sheet 6. In a particular embodiment, cuts 10 through the sheet 6 parallel the direction of high tensile strength of the synthetic sling material may substantially maintain the strength of the synthetic material.

In one embodiment, the longitudinal axis 34 of the sheet 6 ranges from about 2.5 cm to about 45 cm in length, and the perpendicular axis 38 ranges from about 1.0 cm to about 3.0 cm. The sheet is preferably 20 to 30 cm in length and 1 to 3 cm wide, though larger and smaller slings are contemplated depending upon the size of the patient and the surface area of the body part that requires support. The cuts 10 are disposed substantially parallel to the longitudinal axis 34 and the cuts 10 range from about 0.5 cm to about 28 cm in length. In some embodiments, the cuts 10 range from about 0.5 cm to about 1.5 cm in length. The thickness of the sheet 6 (not depicted in the plan view of FIGS. 1, 2, 3, 4, 5, 6A, 6B, 7A, and 7B) can be uniform over the entire piece of the sheet 6 or it can vary at one or more different locations of the sheet 6. The thickness of a material from a mammalian source can range from about 0.01 inches to about 0.2 inches, but typically will be about 0.05 inches. The thickness of a material from a synthetic source may range from about 0.01 inches to about 0.05 inches, but typically will be about 0.035 and a uniform thickness. The material construction may impact the material thickness such that, for example, a weave may have thicker regions where the fibers intersect and the material thickness may not be uniform.

In one embodiment, according to the invention, the sheet 6 may be made of non-synthetic material(s), e.g., mammalian tissue(s), synthetic material(s), or a combination of non-synthetic material(s), and synthetic material(s). One or more mammalian tissues including porcine, ovine, bovine, equine, human cadaveric, or tissue-engineered tissue(s) may be employed to make the sheet 6. The sheet 6 may be derived from omnidirectional tissue(s), tissues where the material has equivalent tensile strength from any direction. Exemplary omnidirectional materials include dermis and/or pericardium. Suitable materials for use in accordance with this invention include a chemically processed acellular human dermis product that preserves, undamaged, the bioactive structural dermal matrix and which is freeze-dried for storage, such as AlloDerm® acellular tissue available form Lifecell (Branchburg, N.J.).

In one embodiment, the non-synthetic material is REPLI-FORM® Tissue Regeneration Matrix, commercially available from Boston Scientific Corporation (Natick, Mass.). The matrix is human dermal allograft that, when placed within the body, serves as a template to facilitate fibroblast mediated regeneration of normal soft tissue. The matrix is formed of banded collagen fibers, elastin, proteoglycans, and vascular plexus. The REPLIFORM® Tissue Regeneration Matrix may be from about 3 cm to about 20 cm in length. In one embodiment, the REPLIFORM® Tissue Regeneration Matrix may be from about 5 cm to about 10 cm in length. In a particular embodiment, the REPLIFORM® Tissue Regeneration Matrix may be about 7 cm in length.

In another embodiment, oriented mammal tissue(s), i.e., tissues having a single direction where the tensile strength of the tissue material is highest, including rectus fascia and/or facia lata may be used for the sheet 6. Suitable cleaned and sterilized oriented human tissue materials may be obtained from tissue banks.

In one embodiment according to the invention, animal tissues may be selected from tissues available from government regulated slaughter houses. Animal tissues may be dehydrated with a dehydrating fluid, such as ethyl alcohol or the like, prior to treatment with chemical crosslinking agents, to allow for improved penetration. The cross-linking agent cross-links collagen in the tissues to make the tissue stronger and reduce the antigenicity of the tissue. Other agents such as pepsin may also be used to further reduce antigenicity. In one embodiment according to the invention, the tissues may be cross-linked by using one or more of the following treatment agents: glutaraldehyde, dialdehyde, glutaraldehyde starch, dialdehyde starch, an epoxy compound or ionizing radiation. Certain processes (such as heat, radiation or pH change) or agents such as halogens, enzymes, organic solvents, detergents, sodium hydroxide, hydrochloric acid, sodium hypochlorite or hydrogen peroxide) may be used to inactivate viruses with and without protein coats during the manufacturing process. The tissue may also be treated with a highly volatile chemical such as, for example, propylene oxide, to assist with the sterilization of the tissue. Sterilization may be accomplished using one or more of the following treatments: glutaraldehyde, alcohol, propylene oxide or irradiation sterilization. The treatment of the tissue, with a combination of these materials and processes, can both cross-link the tissue and render the tissue sterile for implantation inside the body of a patient. Other processing techniques may be suitable, as known in the art, including mechanical and chemical processing steps to affect various characteristics of the tissue (i.e., acellularity, antigenicity, resorbability).

In another embodiment according to the invention, the synthetic sling material may be a solid material, a weave, a braid, a mesh or an alternate material construction. The synthetic material may be a polymer. Suitable polymer sources for the sling 2 may include nylon, polyethylene, polyester, polypropylene, fluoropolymers or copolymers thereof. An exemplary synthetic polyester material suitable for use in the sling 2 according to the invention is available under the trade designation Dacron®, from E.I. du Pont de Nemours and Company (Wilmington, Del.). In another embodiment, suitable synthetic materials include the fluoropolymers polytetrafluoroethylene (PTFE), which has non-melt processible characteristics, and fluorinated ethylene propylene (FEP), which has melt-processible characteristics, both fluoropolymers are available under the trade designation Teflon®, from E.I. du Pont de Nemours and Company (Wilmington, Del.). A suitable PTFE material of solid material construction is available under the trade designation GORE-TEX®, from W. L. Gore & Associates, Inc. (Flagstaff, Ariz.).

In a particular embodiment, the synthetic sling material comprises mesh. The mesh may have any of a number of knits, weaves, braids or non-wovens, such as those described in U.S. Pat. Nos. 5,569,273; 5,292,328; 5,002,551; 4,838,884; 4,655,221; 4,652,264; 4,633,873; 4,520,821; 4,452,245; 4,347,847; 4,193,137; 5,124,136; 3,054,406; and 2,671,444 the disclosures of which are hereby incorporated by reference.

The mesh material may be fabricated from any of a number of biocompatible materials such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials include polyglycolic acid, polylactic acid, and other suitable absorbable synthetic materials. The mesh material may be fabricated from one or more yarns, which yarns may be made from one or more materials. The mesh may be produced according to numerous fabrication processes, and may be designed to permit rapid tissue revascularization and tissue in-growth by having large interstitial spaces. For example, each yarn of the mesh may have void areas between yarn filaments and the fabrication process may create crevices. An exemplary weave is a tricot knit with two yarns per needle. In a preferred embodiment, the mesh is composed of polypropylene monofilament yarns.

In yet another embodiment, absorbable synthetic materials may be suitable for a sling 2 in accordance with the invention. For example, polyglycolic acid (PGA), polylactic acid (PLA), and other available absorbable synthetic materials may be suitable. A PGA material that may be suitable for use in sling 2 is available under the trade designation Dexon®, from American Cyanamid Company (Wayne, N.J.). Other suitable polymeric and non-polymeric synthetic materials may be employed in accordance with the invention.

In another embodiment, combinations of synthetic materials and mammalian tissues may also be used according to the invention. These combinations may include material having a combination of parts, including, for example, parts made of synthetic polymers and parts made of processed animal tissues. Such combinations also include materials that have both synthetic polymers and animal cells that are treated so as to cross-link the collagen or other commonly antigenic fibers in the animal cells.

Tangs (i.e., sharp projections or frayed edges) often form along any edge of the material forming the sling when the material is cut, chopped, torn, frayed or otherwise manufactured. It has been observed that some tangs may be advantageous in some respects, such as serving to anchor the sling in the tissue (particularly in an application where no independent anchoring structure is utilized). However, in other respects, some tangs may erode the adjacent tissue when the sling is inserted into a patient's body. Accordingly, erosion effects may be reduced by smoothing, rounding, or removing some or all of the tangs along the length of the sling. Any process that will smooth, round or remove the tangs to remove their sharp edges is suitable. For example, the tangs may be heat smoothed by burning or melting. Such a heat process causes melting of the sharp tangs back to the woven knot forming a non-tanged section. The non-tanged section may be located on both sides and occupying, for example, about 1 to 4 cm on either side of the perpendicular axis. The tangs may be removed, for example, along a 5, 6, 7, 8, 9 or 10 cm portion of the side of the mesh material.

An exemplary method of making a sling of the invention from a material includes manufacturing a sling material and form a non-tanged section on a portion of a material at the sides and adjacent the perpendicular axis. The sling may be formed from the cutting to size of a larger piece of sling material. The tangs on a portion of each side are unformed, smoothed, rounded or removed (e.g., to the woven knots) to form a non-tanged section. The non-tanged section may span a segment of the sides and have a length up to about 4 cm, but usually at least about 1 cm. The segment is preferably centered on the perpendicular axis. In an alternative embodiment, the non-tanged section may span a segment of sides having a length of 5, 6, 7, 8, 9 or 10 cm. In one version of the method, the tangs are smoothed, rounded or removed by exposing the tangs to a source of heat (i.e., by contact or by bringing the heat source into close proximity to the tangs). In an alternative method, a straight blade edge that is heated to a sufficient temperature to simultaneously cut and smooth the tangs may be employed.

According to one embodiment of the invention, following implantation of a sling 2 in the body of the patient, at least some, and generally all or most, of the cuts 10 provide open areas through the sling 2. Tissue will begin to grow into these open areas. The tissue in-growth secures the sling 2 position inside the patient's body.

Figure 2:
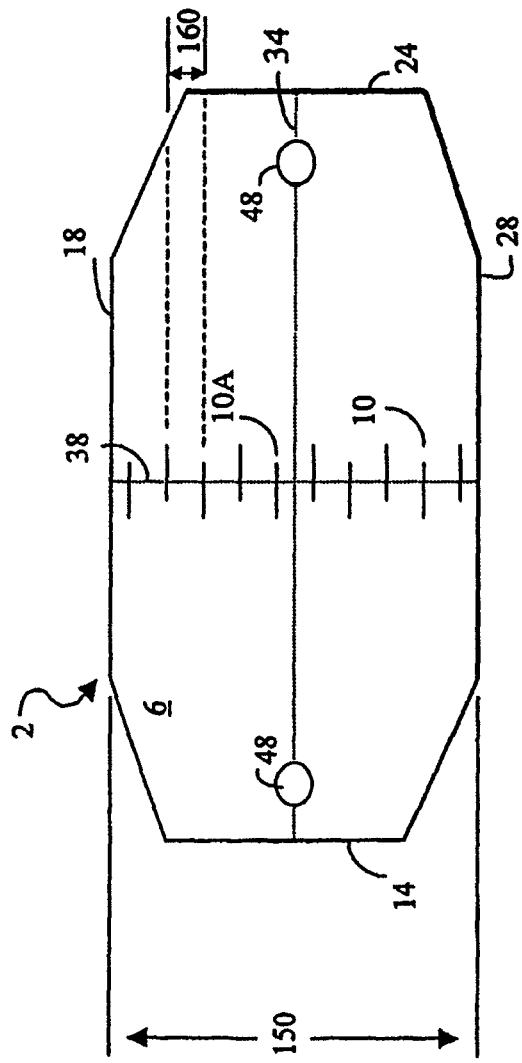
FIG. 2 illustrates a plan view of another embodiment of a substantially rectangular shaped embodiment of a sling in accordance with the invention.

In one particular embodiment illustrated in FIG. 1, the first 1 cm and the last 1 cm of the longitudinal axis 34 do not have any cuts 10. A fastener 46 for securing the sling 2 to an anatomical structure of the patient can be disposed in the 1 cm region at each end of the longitudinal axis 34. Alternatively, as shown in FIG. 2, one or more attachment sites 48, for example, eyelets, may be disposed throughout the sling 2 and located at, for example, the first end portion 14 and the second end portion 24 of the sling. In one particular embodiment illustrated in FIG. 5, the fasteners 46 are, for example, sutures that are disposed on the sling 2 by threading them through the eyelets 48 in the synthetic sheet 6 sling 2. In one embodiment, the fastener 46 is, for example, a suture, clip, staple, anchor. In alternative embodiments, the fastener 46 is pre-attached to the sling 2.

In some embodiments, the cuts 10 are disposed such that the distance between adjacent cuts 160 is equal. The distance between equally distanced adjacent cuts 160 may range from about 5 mm to about 1.25 cm in length, for example. The cuts 10 disposed adjacent and equidistant may be disposed along the perpendicular axis 38 from the first side 18 to the second side 28 of the sling 2. In one embodiment, the cuts 10 are disposed about the region of the sling 2 where the perpendicular axis 38 and the longitudinal axis 34 intersect. A single cut 10 may be employed and it can be disposed at any point along the perpendicular axis 38. The cuts 10 are disposed such that the distance 150 remains substantially constant upon exposure to a tensioning force applied substantially along the longitudinal axis 34 during a medical application (such as a procedure to implant the sling 2 in the body of a patient to treat ISD).

In one embodiment, a sling made of a synthetic material is disposed with cuts 10 that are slits 10A. The unimplanted sling 2 distance 150 is 2.0 cm. After exposure to tensioning force, the implanted sling 2 has a distance 150 that ranges between about 1.6 cm and about 2.0 cm. In an embodiment, as shown in FIG. 2, where the cuts 10 are slits 10A that are disposed along the high tensile strength direction of the synthetic material, the sling 2 distance 150 is maintained closer to the original distance 150, at about 2.0 cm.

In one embodiment, the sheet 6 is derived from the oriented human cadaveric tissue fascia lata, and the cuts 10 are disposed through and along the grain of the sheet 6 made of oriented material. The cuts 10 are disposed on the sheet 6 so that the width of the sheet 6 (at least along the perpendicular axis 38) is maintained at substantially the same distance 150 before, during, and after the application of tensioning force substantially along the longitudinal axis 34 such as would be applied to the sheet 6 during a medical application. Such tensioning force is applied to the sling 2 when, for example, the sling 2 is implanted inside a female patient in a medical procedure designed to treat stress urinary incontinence.

Generally, material derived from mammalian tissue does not have any cuts or open areas. The time period for slings made from mammalian tissue material lacking any cuts or open areas to absorb into the patient host is generally six to twelve months. Likewise, solid, tightly woven, or closely knit absorbable synthetic materials generally do not have open areas. The time period typically required for such synthetic absorbable materials to be absorbed by the patient's body is between about one to about six months. Disposing the cuts 10 through the sheet 6 allows rapid tissue in-growth, which anchors the sling 2 at the location where it was implanted and generally lessens the time it takes for the sheet 6 to absorb into the patient's body and thus lessens the healing process.

On a sling 2 made of mammalian tissue or absorbable synthetic material, the cuts 10 open areas will be absorbed into the area adjacent to the patient's body within a few weeks after implantation. The time period required for the entire sling 2 made from mammalian tissue or absorbable synthetic material to be absorbed by the patient's body may be reduced in proportion to the open surface area on the sling 2. Thus, where cuts 10 are disposed so that sling 2 made of mammalian tissue has fifty percent open surface area, the time period for the sling 2 to be absorbed into the patient's body may be reduced to between about three and twelve months as compared to the minimum six months for mammalian tissue material lacking any cuts.

As shown in FIG. 2, a substantially rectangular sling 2 according to one embodiment of the present invention has cuts 10 that are slits 10A extending through the thickness of the sheet 6. The slits 10A are disposed such that they are alternately offset to the left and to the right of the perpendicular axis 38. As shown, a longer portion of slits 10A extends from the perpendicular axis 38 to the first end portion 14, and this alternates in that the next slit 10A has its longer portion located from the perpendicular axis 38 to the second end portion 24 and so on. Thus FIG. 2 shows an alternating pattern of offset slits 10A. In other embodiments, other patterns are used. In all variations, the cuts 10 are disposed substantially along at least a portion of the perpendicular axis 38.

In one embodiment, the slits 10A are disposed through the sheet 6, and they open upon exposure to a substantially longitudinal tensioning force that is applied to the sling 2 during a medical application. One exemplary medical application is the implantation of the sling 2 into the body of a female patient to treat stress urinary incontinence. The opened slits 10A provide open areas that allow rapid scar tissue formation and tissue in-growth generally. These opened slits 10A permit tissue crosslinking and tissue in-growth into the sling 2 once the sling 2 is secured inside the body of the patient.

The slits 10A are disposed on the sling 2 such that when the sling 2 is implanted inside the patient's body, the slits 10A provide openings that allow tissue in-growth at the site of the damaged portion of the patient's body that the sling 2 is employed to support. In one embodiment, the sling 2 is employed to support a patient's urethra. The slits 10A are disposed on the sling 2 along the perpendicular axis 38 such that when implanted adjacent to the patient's urethra, the open areas allow in-growth to the regions of the urethra that require support. In some embodiments, one or more of the slits 10A are opened when the sling 2 is positioned at an angle surrounding the patient's urethra.

Figure 3:
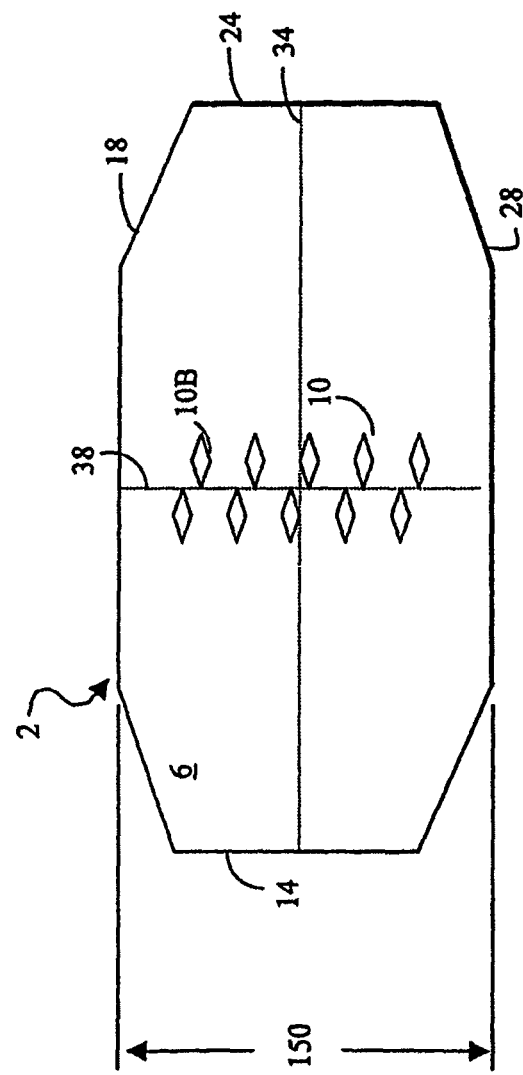
FIG. 3 illustrates a plan view of another embodiment of a substantially rectangular shaped sling in accordance with the invention.

In the embodiment of FIG. 3, a substantially rectangular shaped sling 2 of the present invention has cuts 10 that are apertures 10B. The apertures 10B are disposed about the perpendicular axis 38 such that they are alternately offset to the left and to the right of the perpendicular axis 38. The apertures 10B are disposed about the perpendicular axis 38 as the alternately offset slits 10A were disposed in FIG. 2.

The apertures 10B provide open areas in sling 2 once disposed through the sheet 6. At least some, and usually all, of the apertures 10B remain open upon exposure to tensioning force applied along the longitudinal axis 34 of the sling 2 during the medical application. When, for example, the sling 2 is implanted inside the patient, the apertures 10B open areas generally permit scar tissue to grow into the sling 2. The size, shape, and placement of each of the apertures 10B may be selected to provide a desired surface area when implanted. In one embodiment, the size of the apertures 10B and the aperture 10B location on the sling 2 are selected such that when implanted inside the patient, scar tissue will grow through the apertures 10B to support an adjacent damaged portion of a patient's body. The apertures 10B are shown as diamond shapes in FIG. 3, but other shapes are possible.

According to the invention, the choice of the size, shape, quantity, and location of the cuts 10 and the choice of sheet 6 may be made to maximize open surface area while maintaining the distance 150 substantially constant upon exposure to a surgical tensioning force.

The percentage by which the distance 150 reduces will depend on the number of cuts 10 and the material type 6, whether from mammalian tissue, synthetic material, or a combination of mammalian tissue and synthetic material. The placement of the cuts 10 on the material will also impact the percentage by which the distance 150 may reduce. When, for example, the cuts 10 are formed along the grain of an oriented mammalian tissue, the distance 150 of the sling 2 may be reduced by a lower percentage then if an omnidirectional tissue material were employed.

In one embodiment where the sheet 6 is derived from an oriented tissue and the cuts 10 are disposed along the grain of the sheet 6, when exposed to surgical tensioning force the sling 2 will maintain a substantially constant distance 150. Generally, an oriented material sling 2 will support more cuts 10 while maintaining a substantially constant distance 150 when exposed to the same surgical tensioning force than an otherwise identical sling 2 made of a sheet 6 derived from an omnidirectional tissue material.

Cuts 10 that are apertures 10B generally have a larger open surface area than cuts 10 that are slits 10A, which results in a greater reduction in the perpendicular distance 150 due to more of the sheet 6 stretching in the longitudinal direction upon exposure to tensioning force. Generally, the distance 150 of slings 2 disposed with cuts 10 that are slits 10A will reduce by between about zero and about twenty percent upon exposure to surgical tensioning force and/or when implanted. The implanted distance 150 of slings 2 disposed with cuts 10 that are apertures 10B will generally reduce by between about zero and about fifty percent upon exposure to surgical tensioning force and/or when implanted.

Figure 4:
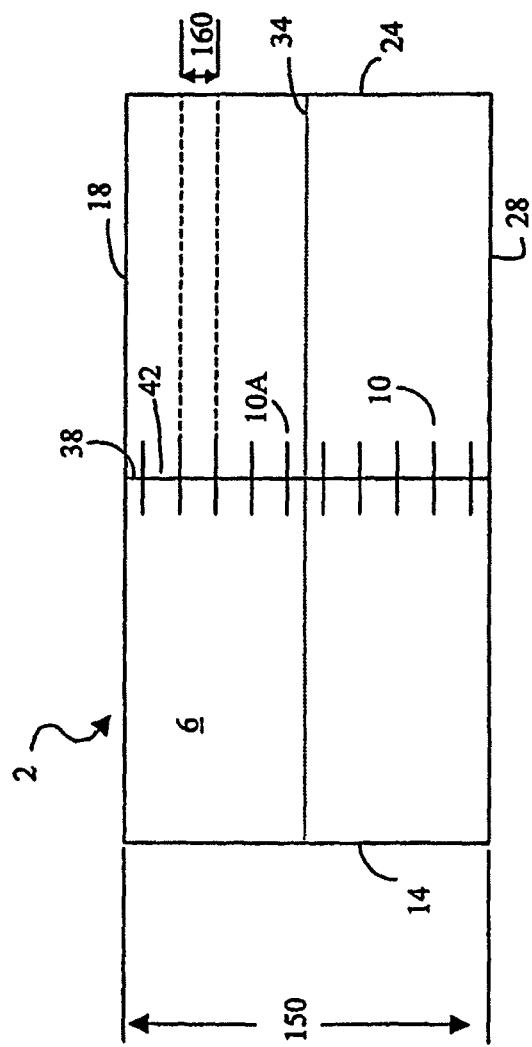
FIG. 4 illustrates a plan view of another embodiment of a rectangular shaped sling in accordance with the invention.

FIG. 4 provides an alternative embodiment where the line 42 is a visual indicator disposed along the perpendicular axis 38 of the rectangular sling 2. The line 42 is a visual guide employed to align slits 10A disposed on the sling 2 with the damaged portion of the patient's body. In one disclosed embodiment, the slits 10A are equal in length, disposed along the perpendicular axis 3 8 and the substantial midpoint of each slit 10A intersects with line 42. The line 42 may be used to evenly align the slits 10A with the portion of the patient's body that the sling 2 is employed to support.

In one particular embodiment, the sling 2 is employed to treat female stress urinary incontinence and is used to support the patient's urethra. During implantation, the surgeon applies tension to the sling 2 and visually aligns line 42 such that it is adjacent to the portion of the patient's urethra requiring support. The slits 2 are selectively disposed about line 42 to target these portions of the patient's urethra. Some or all of the slits 10A disposed on line 42 of the implanted sling 2 provide open areas to the patient's urethra. Some or all of the slits 10A may open when the sling 2 is bent around to surround the patient's urethra. Other slits 10A may open upon exposure to substantially longitudinal tensioning force during the medical application. Very soon after being placed inside the patient's body, scar tissue will begin to grow into the slings 2 open areas to support the targeted portion of the patient's urethra.

Figure 5:
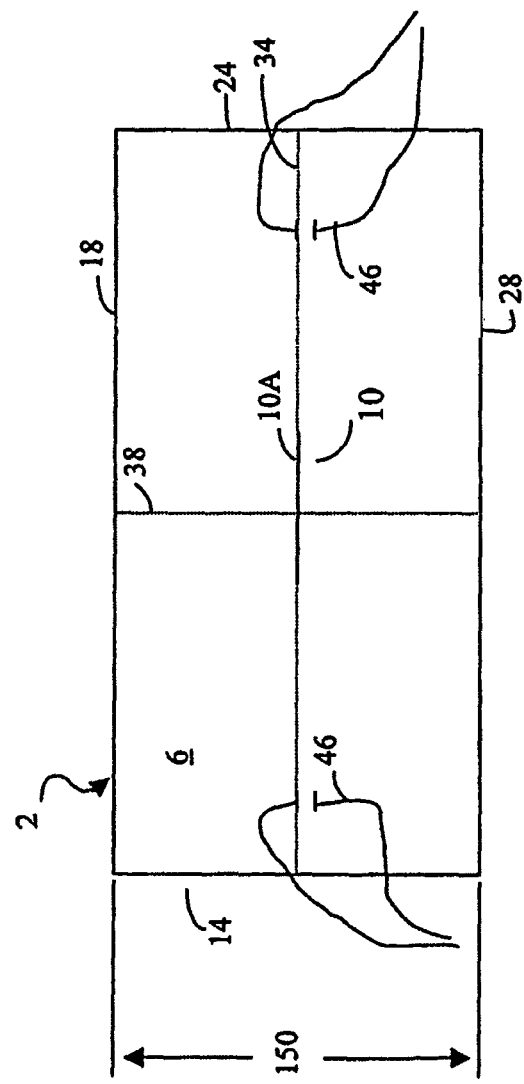
FIG. 5 illustrates a plan view of another embodiment of a rectangular shaped sling in accordance with the invention.

In the embodiment of FIG. 5, the sling 2 has a single cut 10, slit 10A, disposed along the perpendicular axis 38. A surgical fastener 46 is disposed at both the first end portion 14 and the second end portion 24 of the sling 2. The fastener 46, disposed at the first end portion 14, is used to anchor sling 2 to a first anatomical structure in the body of a patient. The fastener 46, disposed at the second end portion 24, is used to anchor sling 2 to a second anatomical structure in the body of a patient.

In one embodiment, the fastener 46 is a suture. In alternative embodiments, the fastener 46 is pre-attached to the sling 2 and may include a clip, a bone anchor, a staple, and/or other suitable fasteners. In a further alternative embodiment, the sling may be secured in an anchorless manner, in which the structure of sling (i.e., tanged portions) provides resistance against movement of the sling in the tissue while tissue in growth occurs.

In a particular embodiment, the sling of FIG. 5 is used to treat a patient suffering from ISD. The surgeon anchors the first end portion 14 to a first anatomical structure, aligns the single cut 10, slit 10A, with the patient's sphincter muscle, and then anchors the second end portion 24 to a second anatomical structure. The cut 10A provides open surface area upon implantation in the patient's body. Soon after implantation, scar tissue begins to grow generally into the open surface area adjacent to the sphincter muscle to compress the sphincter muscle and improve continence. This scar tissue formation quickly maintains the sling 2 in the place where the surgeon positioned it.

The slings 2 of FIGS. 6A and 6B feature two first end portion elongated members 114a and 114b and two second end portion elongated members 124a and 124b extending from the central portion of sling 2. The slits 10A are disposed about the perpendicular axis 38. FIG. 6A has slits 10A that are disposed along the perpendicular axis 38. FIG. 6B has slits 10A that are disposed so that they are alternately offset to the left and to the right of the perpendicular axis 38.

Figure 7A:
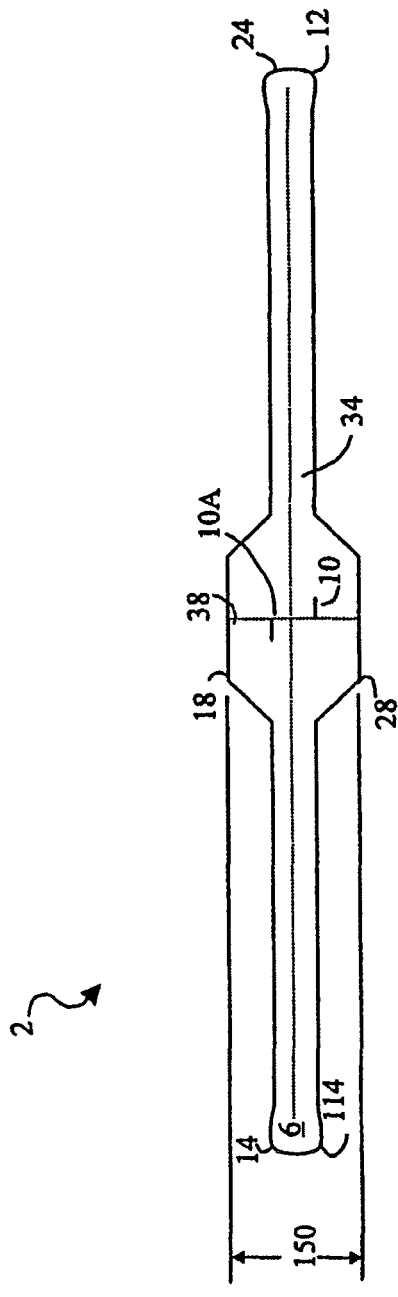
FIG. 7A illustrates a plan view of another embodiment of a sling including elongated end members extending from a central portion of the sling in accordance with the invention.
Figure 7B:
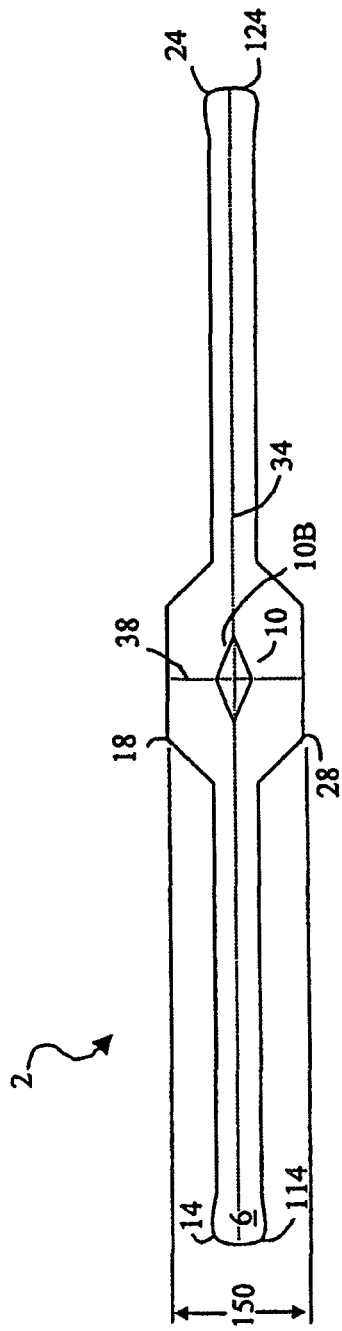
FIG. 7B illustrates a plan view of another embodiment of a sling including elongated end members extending from a central portion of the sling in accordance with the invention.

The slings 2 of FIGS. 7A and 7B feature a first end portion elongated member 114 and a second end portion elongated member 124 extending from the central portion of sling 2. Cuts 10 are disposed about the perpendicular axis 3 8 of sling 2. FIG. 7A has slits 10A that are alternately offset to the left and the right along the perpendicular axis 38. FIG. 7B has a cut 10 that is an aperture 10B disposed at the midpoint of the longitudinal axis 34 and the perpendicular axis 38.

A method of making a sling 2 of the invention (depicted in, for example, FIG. 4) from a sheet 6 includes, in overview, the steps of: providing a sheet 6 in a shape suitable for a medical application and forming one or more cuts 10 substantially along the perpendicular axis 38 of the sheet 6. The sheet 6 includes a first end portion 14 and a second end portion 24, the second end portion 24 is disposed opposite and away from the first end portion 14 along a longitudinal axis 34. The sheet 6 also includes a first side 18 and a second side 28, the second side 28 is disposed opposite and away from the first side 18 by a distance 150 and along a perpendicular axis 38. The perpendicular axis 38 is substantially perpendicular to the longitudinal axis 34, and the perpendicular axis 38 intersects the longitudinal axis 34 at substantially the midpoint of the longitudinal axis 34. Forming one or more cuts 10 disposed substantially along at least a portion of the perpendicular axis 38. The cuts 10 are formed such that the distance 150 remains substantially constant upon exposure to tensioning force applied to the sheet 6 substantially along the longitudinal axis 34 during the medical application.

A first step in making the sling 2 is obtaining sheet 6 in a shape suitable for use in a medical application. Exemplary materials may be obtained from mammalian tissues, synthetic material or a combination of mammalian tissue and synthetic material. Mammalian tissue sources include human cadaveric, tissue-engineered products, porcine, ovine, bovine, equine and/or other tissues. The mammalian material may be omnidirectional, oriented, or a combination of the two.

Omnidirectional tissues include dermis and pericardium. One chemically processed acellular human dermis product that preserves, undamaged, the bioactive structural dermal matrix and which is freeze-dried for storage is suitable for use as the sheet 6 in accordance with this invention. The removal of cells from the otherwise intact dermal matrix reduces the risk of rejection and inflammation and the matrix provides a basis for soft tissue reconstruction. Such an acellular human matrix is available from Lifecell (Branchburg, N.J.) and is referred to as AlloDerm® acellular tissue.

Oriented materials suitable for use in the present invention include human fascia lata and rectus fascia. Cleaned and sterilized oriented human tissue materials may be obtained from tissue banks. Suitable animal tissues may be suitable for use in accordance with the invention after the animal tissues are cleaned, chemically treated, and sterilized according to various methods that are available in the art. Such animal tissues may be available from government regulated slaughterhouses, for example.

Suitable synthetic materials may be a solid material, a weave, a braid, a mesh or an alternate material construction. The synthetic material may be a polymer. Suitable polymer sources may include nylon, polyethylene, polyester, polypropylene, fluoropolymers or copolymers thereof. An exemplary synthetic polyester material suitable for use in according to the invention is available under the trade designation Dacron®, from E.I. du Pont de Nemours and Company (Wilmington, Del.). Other suitable synthetic materials include the fluoropolymers available under the trade designation Teflon®, from E.I. du Pont de Nemours and Company (Wilmington, Del.). Suitable absorbable synthetic materials may be employed in accordance with the invention. Such absorbable synthetic materials include polyglycolic acid (PGA), polylactic acid (PLA), and other available absorbable synthetic materials. A PGA material that may be suitable for use in accordance with the invention is available under the trade designation Dexon®, from Davis and Geck (Wayne, N.J.). Other suitable polymeric and non-polymeric synthetic materials may be employed in accordance with the invention.

Combinations of synthetic materials and mammalian tissues may also be used according to the invention. These combinations may include material having a combination of parts, including, for example, parts made of synthetic polymers and of processed animal tissues. Such combinations also include materials that include both synthetic polymers and animal cells that are treated so as to cross-link the collagen or other commonly antigenic fibers in the animal cells.

The sheet 6 is provided in a shape suitable for a medical application. Suitable shapes of sheets 6 may be rectangular and substantially rectangular. The material may be shaped such that elongated members extend from a central portion of the sheet 6. Other suitable shapes of the sheet 6 include octagonal, trapezoidal, elliptical and hexagonal shapes.

A second step of making the sling 2 is forming one or more cuts 10 in the sheet 6 positioned substantially along at least a portion of the material's 6 perpendicular axis 38. The cuts 10 are disposed so that upon exposure to tensioning force applied substantially along the longitudinal axis 34 of the sheet 6, pursuant to a medical application, the distance 150 remains substantially constant. Multiple cuts 10 may all be formed at the same time. Alternatively, cuts 10 can be formed one at a time. A cut 10 may be formed by extending a straight blade edge through the sheet 6 for the length of the cut 10. The cuts 10 may also be formed by pressing a die in the shape of cut 10 into the sheet 6 to punch out and separate the shape of the punched cut 10 from the sheet 6. For example, a sharpened die in the shape of aperture 10B pressed into sheet 6 will form the aperture 10B in the sheet 6 by punching out and separating the shape of aperture 10B from the sheet 6. Other methods may be employed to form cut(s) in the sheet 6.

In some embodiments, exposing the cuts 10 to heat when forming the cuts 10 or after they are formed in the sheet 6 seals the cuts 10 and prevents the sheet 6 from fraying at the site of each cut 10. Heat sealing the sheet 6 at the site of the cuts 10 may be useful when, for example, the sheet 6 is a synthetic polymer material of solid, woven, braided, mesh or other construction.

The cuts 10 may be sealed ultrasonically, by exposing the cuts 10 to mechanical heat to seal the cuts 10. Alternatively, the cut 10 may be a slit 10A that is made with a straight blade edge that is heated to a sufficient temperature to seal the slit 10A. In one particular embodiment, a sharpened die in the shape of aperture 10B is heated and the aperture 10B is cut and sealed in one step by pressing the heated die into sheet 6 to punch out and form a sealed aperture 10B in the sheet 6.

In one embodiment, one or more of the cuts 10 are slits 10A that extend through the thickness of the sheet 6 for the length of the slit 10A. Alternatively, for example, the slits 10A do not extend through the entire thickness of the material for the length of the slit 10A. However, upon exposure to tensioning force applied during the implantation, the slit 10A may extend through the sheet 6 to provide open surface area through the material. In another embodiment, as disclosed in FIG. 3, one or more of the cuts 10 is an aperture 10B. Upon exposure to tensioning force applied during the medical application, one or more of the apertures 10B remain open.

An alternative embodiment, as shown in FIG. 4, includes the step of forming a line 42 substantially along at least a portion of the perpendicular axis 38 of the sheet 6. The line 42 may be formed by, for example, applying surgical ink along the perpendicular axis 38 of the sheet 6.

Another embodiment, as disclosed in FIG. 5, includes the step of disposing one or more fasteners 46 at the first end portion 14 of the sheet 6. Thereafter, one or more fasteners 46 may be disposed at the second end portion 24 of the sheet 6. Fasteners 46 disposed on the sling 2 include sutures, bone anchors, staples, clips, and other suitable fasteners. In one particular embodiment, the fasteners 46 are sutures threaded through and secured to the sheet 6 at locations where slits 10A are not present for the first and last 1 cm of the longitudinal axis 34.

In an alternative embodiment, as shown in FIG. 2, one or more eyelets 48 are formed in the sheet 6 and the fasteners 46 are sutures threaded through and secured to the eyelets 48. The eyelets 48 may be formed through the material by pressing a die in the shape of the eyelet 48 into the material and punching the shape of the eyelet 48 out of the sheet 6. In one particular embodiment, the sheet 6 is a synthetic braided material and a heated die in the shape of eyelet 48 is pressed into the sheet 6 to form the sealed eyelet 48, thus preventing the sheet 6 from fraying at the site of the eyelet 48.

The sling 2 may be sterilized and packaged in a sterile holder. The packaging conditions may be dry and the package protective of the sling 2 during transport and storage. The packaging may be designed to protect the sheet 6 of the sling 2 from ultra-violet light to prevent damage. The sling 2 disclosed herein is packaged in a shape and size suitable for its intended purpose. Upon opening the protective package, the sling 2 may be hydrated, if necessary, with, for example, saline solution, and thereafter implanted in the patient without any additional alteration by the surgeon performing the surgical procedure. In an embodiment where, for example, the sling 2 made of mammalian tissue material is employed, the sling 2 is hydrated in saline solution prior to implantation.

In one embodiment, in accordance with the invention, a method of treating a damaged portion of a patient's body employs the sling 2. The method includes, in overview, providing the sling 2, as described herein. Securing the first end portion 14 of the sheet 6 of the sling 2 to a first anatomical structure in the body of the patient. Applying tensioning force substantially along the longitudinal axis 34 of the sheet 6. Securing the second end portion 24 of the sheet 6 to a second anatomical structure in the body of the patient. The perpendicular axis 38 of sling 2 is positioned so that it lies substantially along a portion of the patient's body. The one or more cuts 10 disposed along the perpendicular axis 38 are disposed such that the distance 150 remains substantially constant with the sheet 6 secured. Supporting a damaged portion of the patient's body with the secured sheet 6. In some embodiments, the sheet 6 evenly distributes pressure on a damaged portion of a patient's body. Alternatively, the sling may be secured in an anchorless manner, in which the structure of sling (i.e., tanged portions provides resistance against movement of the sling in the tissue while tissue in growth occurs, without the use of an independent anchoring structure.

In one particular embodiment, the sling is employed to treat a female patient suffering from stress urinary incontinence. Physiological conditions that cause stress urinary incontinence include ISD, bladderneck hypermobility, and a combination of the two conditions. When a sling is employed to treat these conditions, it may be used to provide support to the patient's urethra. Where the physiological condition is ISD, the sling may be implanted to improve improper coaptation of the urethral sphincter. Alternatively, where the condition is hypermobility, the sling may be implanted to support, elevate or "back stop" the midurethra. In the patient who suffers from a combination of ISD and hypermobility, a sling 2 may be implanted to support one or both of these sites.

Methods of sling delivery and implantation to treat female stress incontinence include transvaginal, transabdominal, supra-pubic, pre-pubic, and transobturator approaches, or some combination of these procedures. Preoperatively, according to these sling delivery methods, the patient receives broad spectrum antibiotics, such as gentamicin and ampicillin. The patient is placed in the dorsal lithotomy position and regional or general anesthesia is administered. Preparation of the patient may include isolation of the anus with a stapled towel or plastic drape. A Foley catheter is placed.

In the transvaginal method, a midline incision is made in the upper vaginal wall beneath the bladdemeck, such as at the urethro-vesical junction. Starting adjacent to the bladder neck on either side of the urethra, a 1 cm incision is made through the anterior vaginal wall approximately 1 cm lateral to and parallel to the midline of the urethra. The vaginal wall is retracted to allow access to the endopelvic fascia. The surgeon then inserts an instrument such as surgical scissors through the incision in the upper vaginal wall and bluntly dissects the tissue on both sides of the urethra to create a pocket for the sling.

The pocket can also be created and the sling can be inserted using a variety of other minimally invasive instruments/methods including the transvaginal, hiatal and percutaneous approaches disclosed in U.S. Pat. No. 6,053,935 entitled "Transvaginal Anchor Implantation Device" issued Apr. 25, 2000, U.S. patent application Ser. No. 09/023,965 entitled "Percutaneous and Hiatal Devices and Methods for Use in Minimally Invasive Pelvic Surgery" filed Feb. 13, 1997, and U.S. Pat. No. 6,099,547 entitled "Method and Apparatus for Minimally Invasive Pelvic Surgery" issued Aug. 8, 2000, which are incorporated herein by reference.

In one embodiment, the sling is secured to the pubic bone with a suture attached to a bone anchor. Referring to FIG. 8A, the sling 2 is implanted inside the patient and the first end portion 14 and the second end portion 24 of the sheet 6 are secured to the pubic bone 230. The sling 2 is similar to the sling described above and shown in FIG. 4. The sling 2 is a rectangular sling made of mammalian material, with a line 42, a visual indicator, disposed along the perpendicular axis 38. The slits 10A are disposed along the line 42. The sling 2 may be positioned between the urethra 210 and the exterior of the anterior vaginal wall 200. According to the anatomical defects of the patient and the preference of the physician, the placement of the sling 2 supports, elevates, or provides a "backstop" for the urethra 210. A variety of instruments/methods may be used to secure the sling 2 to the bone 230 including the bone anchor disclosed in the U.S. Pat. No. 6,053,935 entitled "Transvaginal Anchor Implantation Device," issued Apr. 25, 2000, the disclosure of which is hereby incorporated by reference.

An anchor implantation device is introduced through the opening in the vaginal wall 200. The leading edge of the anchor implantation device is pressed through the anterior vaginal wall incision to the side of the bladder neck, and inserted into the inferior edge of the posterior aspect of the pubic bone. In some embodiments, the anchor implant site is located lateral to the symphysis pubis and cephalad to the inferior edge of the pubic bone. In one particular embodiment, the anchor implant site is located approximately 1 cm lateral to the symphysis pubis and 1 cm cephalad to the inferior edge of the posterior aspect of the pubic bone.

After the anchor is driven into the pubic bone 230, the anchor implantation device is withdrawn and removed leaving the two free ends of suture exiting the endopelvic fascia and trailing the two free ends of the suture from the vaginal wall 200 incision. The above procedure is repeated on the opposite side of the urethra 210 to implant a second anchor.

A pre-sized sling 2 may be selected to suit the size of the patient. The sling 2 is removed from its sterile packaging. In some embodiments, the surgeon will remove excess portions of the sling 2 to suit the patient. In an embodiment where the sheet 6 is made from mammalian tissue, the surgeon may cut off excess portions of the sling 2 without further treatment of the sheet 6 to prevent fraying. In embodiments where the sheet 6 is made from a synthetic material, the surgeon may heat seal the edge where excess sheet 6 was removed from the sling 2 to prevent the material from fraying. Thereafter, the sling 2 is hydrated in preparation for implantation. Water, saline, or other solutions may be employed to hydrate the sling. Furthermore, the hydrating solution may include an antimicrobial and/or an antibiotic.

The sling 2 is positioned in the pocket formed under the urethra 210. The free ends of suture from the two anchors on each side of the urethra 210 are then tied to the first end portion 14 and the second end portion 24 of the sling 2. The sutures are then tied off with the appropriate amount of tension to support the urethra 210. In one particular embodiment, slits 10A are disposed about line 42 on sling 2 and line 42 is aligned with the portion of the patient's urethra 210 requiring support. Upon implantation, at least some of the slits 10A will provide open areas to patient's urethra. The vaginal wall 200 incision is then closed.

In an alternative transvaginal procedure, the sling is implanted inside the patient as depicted in FIG. 8B. The sling 2 is similar to the sling 2 described above and shown in FIG. 4. The sling 2 is rectangular in shape and is comprised of mammalian tissue. The sling has both a visual indication line 42 and slits 10A disposed along the perpendicular axis 38.

The sling 2 is implanted inside the patient and the first end portion 14 and the second end portion 24 of the sheet 6 are secured to the muscular and/or fascial urethral supports 220. The sling 2 is located between the urethra 210 and the exterior of the anterior vaginal wall 200. The sling 2 supports the urethra 210.

The pocket is formed as described above. The sling 2 size may be pre-selected to suit the patient. The surgeon selects the sling size according to the patient size and area the sling 2 is employed to support. The sling 2 is removed from the sterile packaging, any excess portions of the sling 2 are cut off to suit the patient and, if necessary, the sling 2 is sealed to prevent fraying where portions of sheet 6 were removed from the sling 2. Thereafter, water, saline, an antimicrobial and/or an antibiotic solution, or other solutions are employed to hydrate the sling 2 in preparation for implantation.

A suture is attached to the first end portion 14 of the sling 2. The suture is threaded through a surgical needle and is introduced inside the patient's body through the opening in the vaginal wall 200. The surgical needle and suture are pressed through the muscular and fascial urethral support 220. The suture anchors the sling 2 to the muscular and fascial urethral support 220. Once the first end portion 14 of sling 2 is anchored to the anatomical structure, the needle is detached from the suture. The surgeon then applies tension to the sling 2 and visually aligns line 42, thereby aligning the slits 10A, with the portion of the patient's urethra requiring support. Thereafter, the above procedure is repeated on the opposite side of the urethra 210 to anchor the second end portion 24 of sling 2 to the muscular and/or fascial urethral support 220. The surgeon confirms that an appropriate level of tension is applied to the sling 2 to support the patient's urethra. Some or all of the slits 10A will provide open areas to the patient's urethra upon implantation inside the patient's body. The vaginal wall 200 incision is then closed.

In alternative embodiments, the sling is secured to the body of the patient without the use of anchors. In a particular embodiment, the sling is delivered and implanted through a transvaginal procedure. A track is formed through abdominal incisions behind the pubic bone to the vagina. The sling is introduced laterally along the track and on either side of the mid-urethra. In another embodiment, the sling is delivered and implanted through a supra-pubic procedure. The track is formed through abdominal incisions behind the pubic bone to the vagina. The ends of the sling are drawn back up through the track to place the sling looped underneath the mid-urethra. In yet another embodiment, the sling is delivered and implanted through a pre-pubic procedure. In this procedure, the track is formed in front of the pubic bone. The ends of the sling are drawn back up through the track to place the sling looped underneath the mid-urethra. In yet another embodiment, the sling is delivered and implanted through a trans-obturator procedure. The track is formed from each of the obturator foramen to the vagina. The sling is drawn back through the tracks from the vagina, forming a shallow loop or hammock underneath the urethra.

In an alternative embodiment, the sling 2 is secured to the body of the patient with a sutureless fastener. Exemplary fasteners that may be used include staples, bone anchors and clips. In another embodiment, the slings shown in FIGS. 1, 2, 3, 4, 5, 6A, 6B, 7A, 7B, 8A and 8B can be secured to the body of the patient using a number of fasteners that include sutures, clips, bone anchors and staples.

The placement of sling 2 relative to the urethra varies according to the condition being treated. Where the condition being treated is bladderneck hypermobility, the sling may be implanted to support, elevate or "back stop" the midurethra and the distal urethra. The sling may be implanted to stabilize or kink the urethra and improve urethral closing pressure, thereby improving continence.

Generally, the implanted distance 150 of slings 2 disposed with slits 10A will reduce by between about zero and about twenty percent. The percentage by which the distance 150 reduces upon exposure to surgical tensioning force will depend on the number of slits 10A and the material type 6, whether from mammalian tissue, synthetic material, or a combination of mammalian tissue and synthetic material. The placement of the slits 10A on the material will also impact the percentage by which the distance 150 may reduce. When, for example, the slits are formed along the grain of an oriented mammalian tissue or along the high tensile strength direction of a synthetic material, the distance 150 may be reduced by a lower percentage then if an omnidirectional tissue material or a synthetic with equivalent tensile strength at all directions were employed.

Figure 9A:
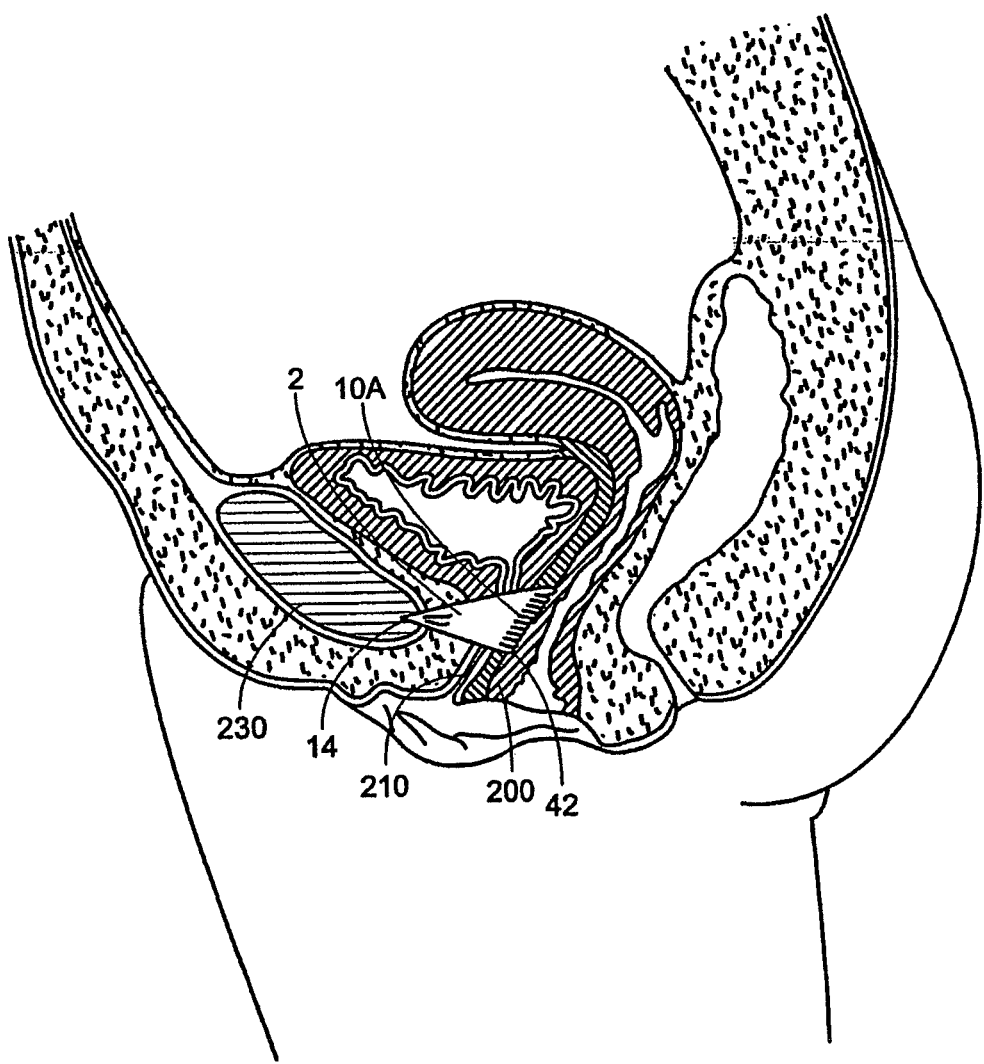
FIG. 9A is a sagittal section of a female pelvis illustrating the location of a sling similar to the sling of FIG. 4 relative to the mid-urethra and distal urethra and anchored to the inferior edge at the posterior aspect of the pubic bone.
Figure 9B:
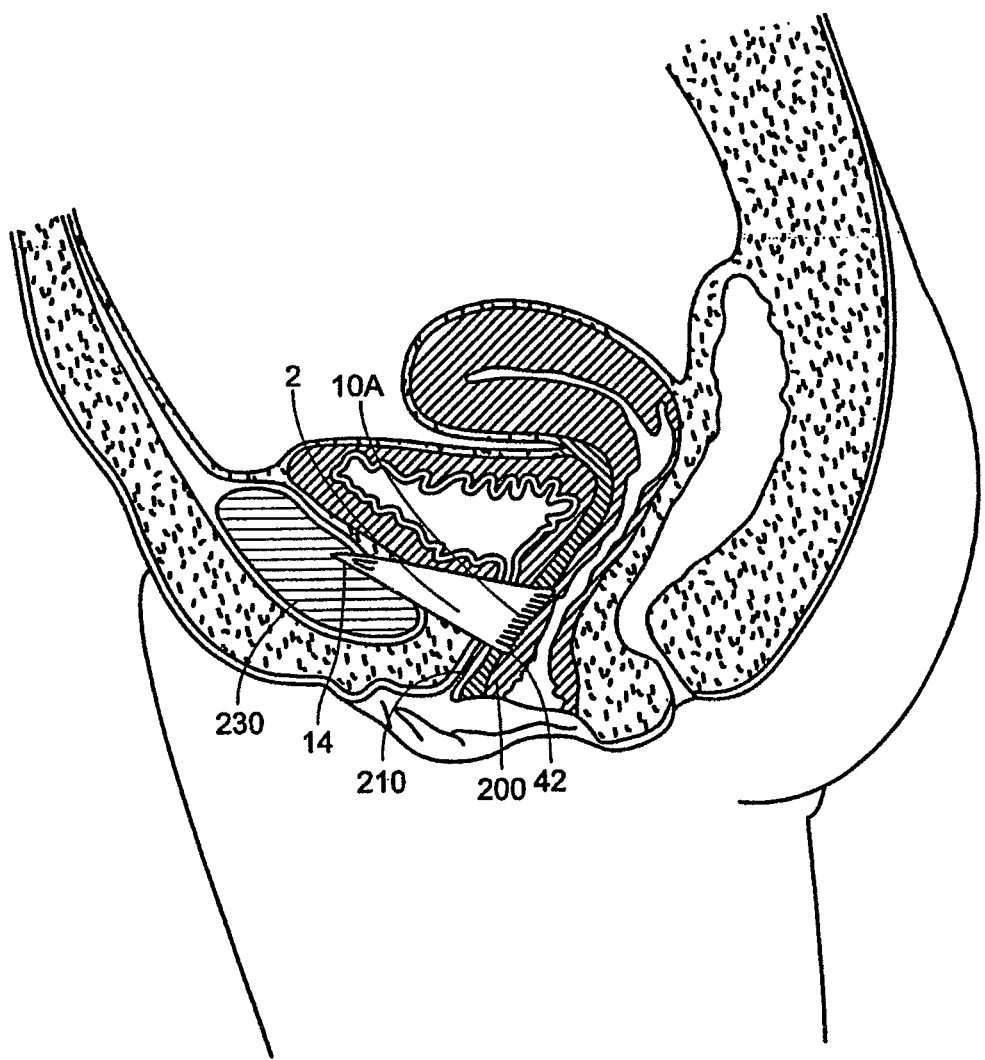
FIG. 9B is a sagittal section of a female pelvis illustrating the location of a sling similar to the sling of FIG. 4 relative to the mid-urethra and distal urethra and anchored to the pubic bone between the superior and the inferior edge on the posterior side of the pubic bone.
Figure 9C:
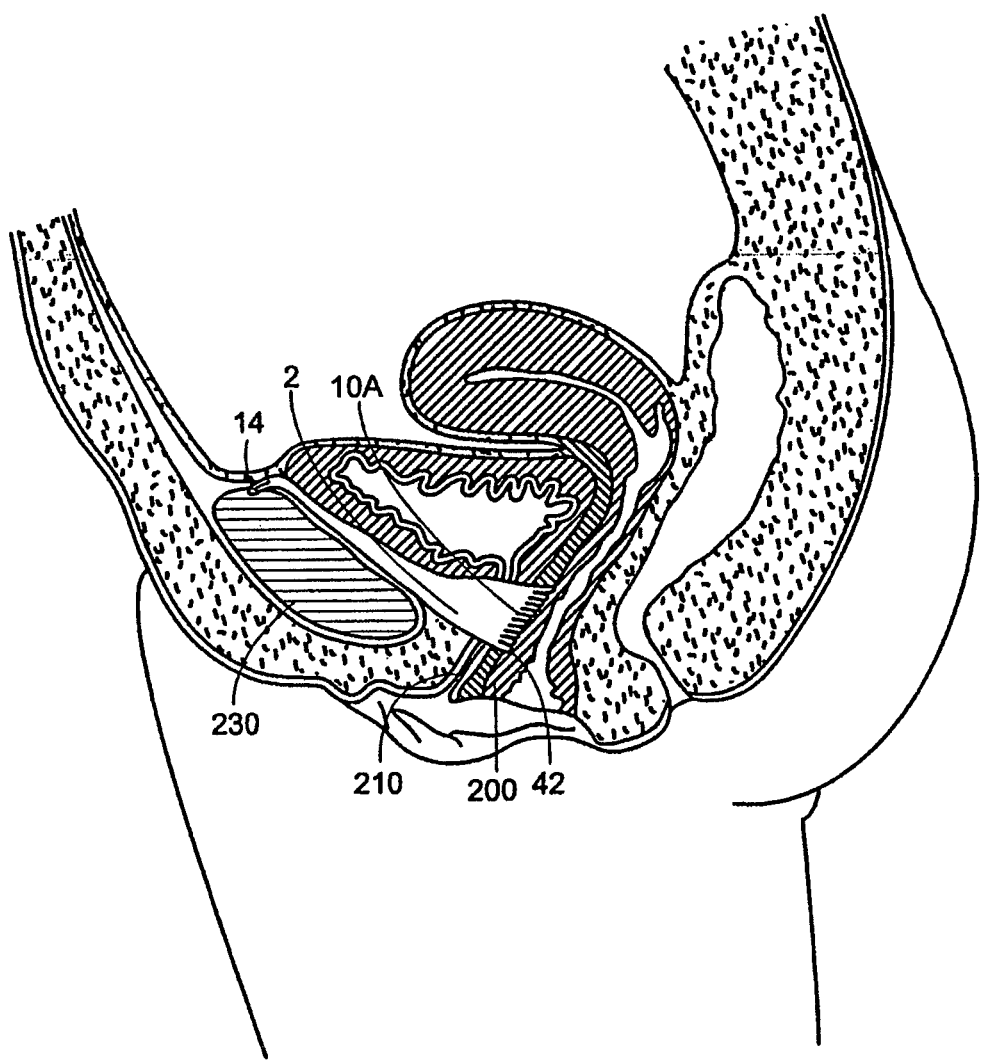
FIG. 9C is a sagittal section of a female pelvis illustrating the location of a sling similar to the sling of FIG. 4 relative to the mid-urethra and distal urethra and anchored to the pubic bone at the superior end of the pubic bone.

FIGS. 9A-9C each provide a sagittal section of a female pelvis illustrating one location of the sling 2 relative to the mid-urethra and distal urethra and anchored to the pubic bone 230. In some embodiments, the sling is positioned mid-urethrally to treat hypermobility.

In FIG. 9A, the sling 2 is anchored to the inferior edge of the public bone 230. The sling 2 may be implanted via the transvaginal procedure described above and shown in FIG. 8A. As shown in FIG. 9B, the sling 2 may also be anchored between the superior and inferior edge of the posterior aspect of the pubic bone 230 at the mid-point or lower toward the inferior edge of the pubic bone 230. The sling 2 may also be implanted via the above referenced transvaginal procedure shown in FIG. 8A.

As shown in FIG. 9C, the sling 2 may be anchored to the anterior side of the superior end of the pubic bone 230. In some embodiments the sling is anchored to the pubic tubercles. The sling 2 may be implanted by employing a percutaneous approach to anchor the sling in the position shown in, for example, FIG. 9C.

The sling of FIGS. 9A-9C is similar to the sling 2 of FIG. 4. In one particular embodiment, the sling 2 depicted in FIG. 4 is made of omnidirectional mammalian tissue material with slits 10A disposed therethrough and the unimplanted distance 150 of the sling 2 is about 2 cm. During implantation, the sling 2 is exposed to substantially longitudinal tensioning force. When implanted, the sling 2 distance 150 will reduce by about twenty percent and the implanted sling will have a distance 150 of about 1.6 cm, thereby maintaining a substantially constant distance upon exposure to substantially longitudinal tensioning force applied to the sheet 6 during the medical application.

In one particular embodiment, the slits 10A are disposed about the line 42 on sling 2. The line 42 is employed to visually align the sling 2 with the patient's midurethra and distal urethra.

In one embodiment, the sheet 6 of sling 2 evenly distributes pressure on the urethra. In another embodiment, the sling 2 evenly distributes pressure on the midurethra without applying pressure to other portions of the urethra.

Upon implantation inside the patient, some or all of the slits 10A provide open areas to the mid-urethra and distal urethra. Some of the slits 10A may become open when the slits 10A are bent around to surround the patient's urethra during implantation. Very soon thereafter, cells infiltrate the open areas of the sling 2 and tissue growth begins. The tissue on both sides of the sling 2 cross communicates such that tissue from both the anterior vaginal wall 200 and urethra 210 grows into the open areas on the sling 2 that they surround. This scar tissue growth provides support to the portions of the mid-urethra and the distal urethra adjacent to the open areas. This tissue growth also secures the sling 2 at the site of implantation, thus improving urethra closing pressure and patient continence.

Within a few weeks of implantation, the area where the slits 10A are on sling 2 made of mammalian tissue material will be absorbed into the portion of the patient's body adjacent to the slits 10A. The time period required for the entire sling 2 made from mammalian tissue material to be absorbed by the patient's body may be reduced in proportion to the open surface area on the sling 2. Thus, where slits 10A provide the implanted sling 2 with fifty percent open surface area, then the time period for the sling 2 to be absorbed into the patient's body may be reduced to between about three and twelve months compared to the minimum six months for mammalian tissue material lacking any cuts. The sling 2 embodied FIG. 4 may be absorbed by the patient's body within a period of between about five and about twelve months.

Figure 10:
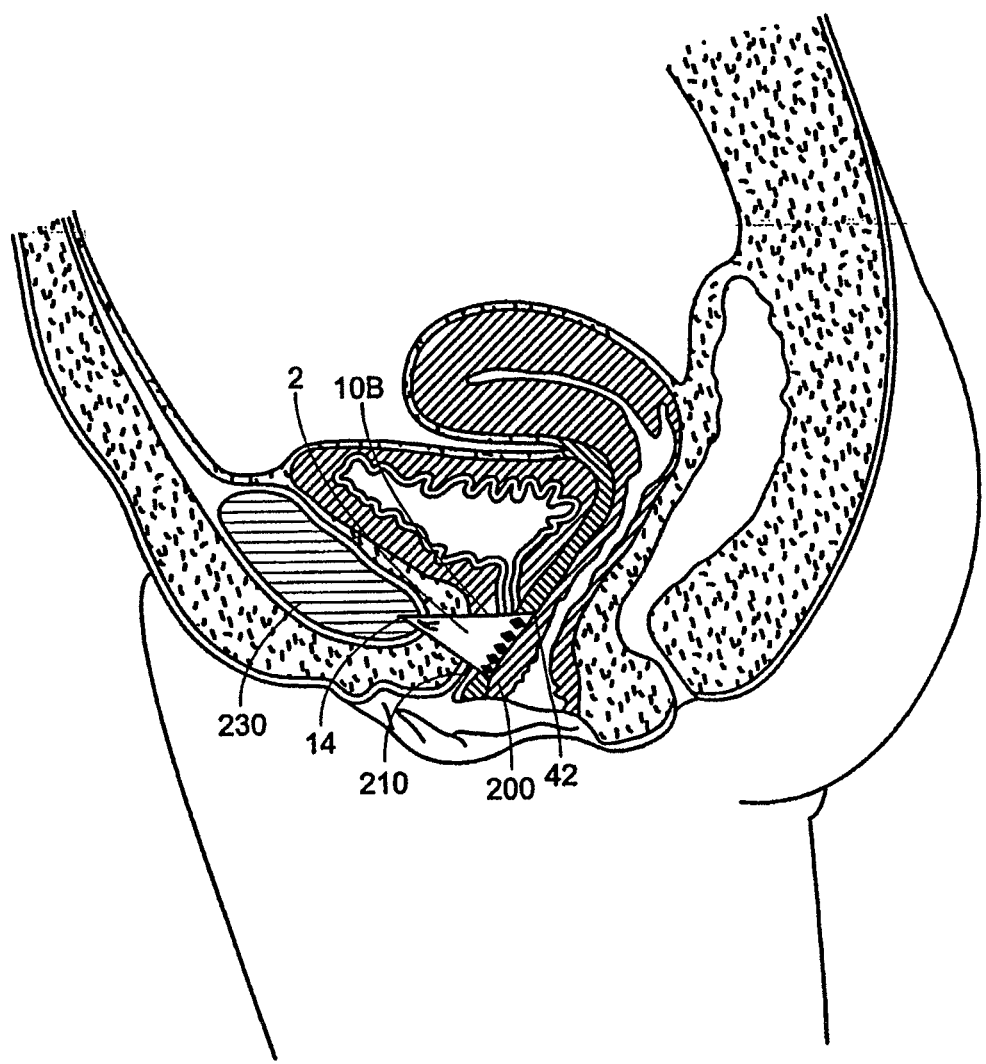
FIG. 10 is a sagittal section of a female pelvis illustrating the location of the sling similar to the sling of FIG. 3 relative to the bladdemeck, sphincter (not shown), and the urethra and anchored to the pubic bone.

In some embodiments, where the condition being treated is ISD, the sling may be implanted to support the distal bladder neck, the sphincter muscle, and the urethra in order to improve improper coaption of the urethral sphincter. FIG. 10 is a sagittal section of a female pelvis illustrating the location of the sling relative to the bladdemeck, sphincter (not shown), and the urethra and anchored to the pubic bone 230. The sling 2 is implanted to treat ISD. The sling 2 of FIG. 10 may be implanted via the transvaginal procedure shown in FIG. 8A. In the treatment of ISD the sling applies direct pressure to the urethra.

The sling of FIG. 10 is similar to the sling 2 described above and shown in FIG. 3, where the sling 2 is disposed with apertures 10B. Generally, the implanted distance 150 of the sling 2 disposed with apertures 10B will reduce by between about zero and about fifty percent. The percentage by which the distance 150 reduces upon exposure to surgical tensioning force will depend on the number of apertures 10B and the type of sheet 6, whether from mammalian tissue, synthetic material, or a combination of mammalian tissue and synthetic material. The size of the apertures 10B and their placement on the sheet 6 will also impact the percentage by which the distance 150 may reduce. When, for example, the apertures 10B are formed along the grain of an oriented mammalian tissue or along the high tensile strength direction of a synthetic material, the distance 150 may be reduced by a lower percentage then if an omnidirectional tissue material or a synthetic with equivalent tensile strength at all directions were employed.

In one embodiment the sling 2 depicted in FIG. 3 the sling 2 is made of, for example, omnidirectional mammalian tissue material with apertures 10B disposed therethrough. The unimplanted distance 150 of sling 2 is about 2 cm. During implantation, the sling 2 is exposed to substantially longitudinal tensioning force. When implanted, as shown in FIG. 10, the sling 2 will have a distance 150 of about 1.2 cm, thereby maintaining a substantially constant distance upon exposure to substantially longitudinal tensioning force applied to the sheet 6 during the medical application.

The distance 150 of the sling 2 made of omnidirectional mammalian tissue sheet 6 depicted in FIG. 10 and 3 may be reduced by a higher percentage than the sling 2 depicted in FIGS. 9A-9C and 4 made of a sheet 6 of the same material. The distance 150 of sling 2, shown in FIG. 3, may be reduced by a higher percentage because the apertures 10B create a greater open surface area. The apertures 10B may result in more stretching of sheet 6 in the longitudinal direction reducing the distance 150 more then the open surface area of the slits 10A, shown in FIG. 4.

The apertures 10B are disposed about the line 42 on sling 2. The line 42 is visually aligned with the patient's bladdemeck, sphincter muscle, and urethra. In one embodiment, the midpoint of the perpendicular axis 38 distance 150 is located adjacent to the urethral sphincter muscle, the first side 18 is adjacent to the distal bladdemeck, and the second side 28 is adjacent to the urethra. In one embodiment, the sheet 6 of sling 2 evenly distributes pressure on the patient's bladdemeck, sphincter muscle, and urethra. In another embodiment, the sheet 6 evenly distributes pressure on the sphincter muscle alone without applying pressure to the bladdemeck and urethra.

Upon implantation, some or all of the apertures 10B maintain an open surface area. Very soon after implantation, tissue begins to grow into the open areas on the sling 2. The tissue on both sides of the sling 2 cross communicates, whereby the tissues from the anterior vaginal wall 200 and urethra 210 and bladdemeck grow into the open areas. This tissue growth provides support to urethral sphincter muscle, urethra, and bladdemeck adjacent to the open areas. This tissue in-growth also secures the sling 2 at the site of implantation. The tissue in-growth will improve coaption of the urethral sphincter, which will improve patient continence.

In an embodiment where the sling 2 is made of mammalian tissue, the area where the apertures 10B provide open areas on the sling 2 will be locally absorbed into the body of the patient, into the urethral sphincter muscle, urethra, and bladdemeck, within a few weeks after implantation. The time period required for the sling 2 to be absorbed by the patient's body may be reduced in proportion to the open surface area on the sling 2 provided by the apertures 10B disposed through the sling 2. Thus, if fifty percent of the sling 2 provides open surface area when implanted inside the patient's body the time period to absorb may be reduced to between about three months and about twelve months. The sling 2 shown in FIG. 3 that is made from mammalian tissue sheet 6 may be absorbed by the patient's body within a period of between about four and about twelve months.

In the combination transvaginal and transabdominal method, the sling is introduced transvaginally, through insertion into pocket through the upper vaginal wall, as described above. Either before or after creating the pocket, an anchor is introduced into the pubic bone 230 for fixation of suspensory sutures, with or without predrilling a hole in the pubic bone. For instance, the anchor is introduced using an anchor implantation device of a type such as that illustrated in FIGS. 15-19 of U.S. Pat. No. 5,766,221, entitled "Bone Anchor Implantation Device", issued Jun. 16, 1998, which is incorporated herein by reference. Anchor sites are located by placing the anchor implantation device on the body over the area of the pubic bone after visualization or digital palpation over the bone. The surgeon then extends the bone probes distally until both probes have made contact with the pubic bone. One or more anchors are implanted into the tubercle portions of the pubic bone at each side of the urethra. The anchor preferably has a suture secured thereto prior to implantation of the anchor into the pubic bone so that a first suture end and a second suture end extend from the implanted anchor after removal of the anchor driver.

The surgeon selects the sling 2. The above described sling 2 comprises sheet 6 disposed with cuts 10 substantially along at least a portion of the perpendicular axis 38. In some embodiments, the sling 2 has a line 42 disposed substantially along at least a portion of the perpendicular axis 38.

An incision is made in the anterior vaginal wall and a pocket is formed as described above. A suture passer is introduced inside the patient's body through the opening in the vaginal wall. Thereafter, the surgeon attaches the sutures to the sling 2. In alternative embodiments, the sutures are pre-attached to the sling 2 of the invention. This step is unnecessary in embodiments were a suture is pre-attached to the sling 2 of the invention, as in FIG. 5, and in sutureless embodiments. After securing the sutures to the sling, the first end of the suture is captured by the suture passer and passed through the body.

In one embodiment, the one or more of the sutures can be laterally attached to anatomical support structures other than the pubic bone, for example, the ileal pectineal ligament (termed Cooper's ligament), the arcus tendinous fascia pelvis, or the pubococcygenous muscle complex. In one particular embodiment, the first end portion 14 of the sling 2 is secured to the pubic bone and the second end portion 24 is attached to the arcus tendinous fascia pelvis (termed the White Line).

In order to minimize postoperative urinary blockage caused by excessive tension, suture tension is regulated by tying the first and second ends of the sutures across a suture tensioner of a type, for example, illustrated in and described with respect to FIGS. 46-49 of U.S. Pat. No. 5,611,515 entitled "Bladdemeck Suspension Procedure", issued Mar. 19, 1997, and the U.S. patent application Ser. No. 09/184,468 entitled "Transvaginal Suture Spacer Devices and Methods of Use", filed Nov. 2, 1998 (both of which are incorporated herein by reference). The suture tensioner is thereafter removed and the position of the sling 2 is reconfirmed prior to closing the vaginal and suprapubic wounds. Transabdominal surgical methods may also be employed to implant the sling 2 in accordance with the invention.

In one embodiment of the invention, non-synthetic material is attached to or wrapped around at least a portion of the synthetic mesh to form the structure of the sling. The non-synthetic material may wrap around at least a portion of the sheet. The non-synthetic material may also completely encompass at least a portion of the sheet. In various embodiments, the non-synthetic material is free floating about the sheet.

When placed within the body of a patient, the non-synthetic material may be disposed adjacent to the urethra. In another embodiment, the non-synthetic material extends to each side of an endopelvic fascia when the sling is placed within the body.

By combining a synthetic material with a non-synthetic material, erosion of body tissue is reduced or eliminated. Without wishing to be bound to a particular theory, it is believed that the interaction of the synthetic material comprising the sling with body tissue may cause erosion into the body. In particular, it has been observed that synthetic polymers may cause erosion into the urethra and vagina. The incorporation of a non-synthetic material, for example, REPLIFORM® Tissue Regeneration Matrix or other suitable animal sources of tissue, into the sling, preferably in the center of the sling, may reduce erosion. Moreover, the non-synthetic material, once placed within the body, will promote fibroblast development of normal body tissue and tissue in-growth. The slings shown in FIGS. 11-20 include a non-synthetic material attached to or wrapped around a synthetic mesh material. These figures depict numerous manners by which to attach to or wrap the non-synthetic material around the mesh; however, the invention envisions other methods of attaching the matrix to the mesh.

Figure 11A:
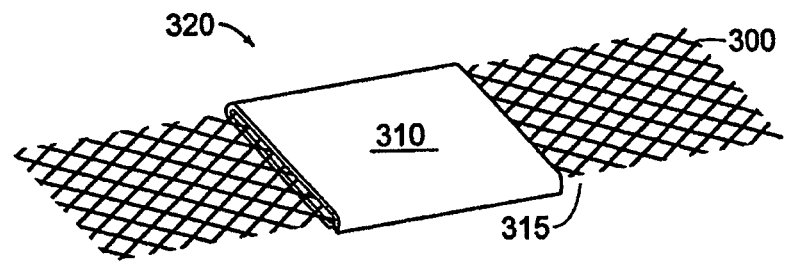
FIG. 11A illustrates a partial perspective view of a sling in accordance with the invention, where the non-synthetic material wraps around a portion of the synthetic mesh material.
Figure 11B:
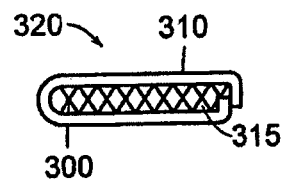
FIG. 11B illustrates a side view of the sling of FIG. 11A.

FIGS. 11A and 11B depict an embodiment of a sling 320 in accordance with the invention. As shown, the non-synthetic material 310 wraps around a portion of a length and a width of the mesh sheet 300. In one embodiment, the non-synthetic material 310 is crimped along one length-wise end 315. Alternatively, the non-synthetic material 310 could be crimped on both ends. The non-synthetic material 310 is free floating about the sheet 300, because the non-synthetic material 310 is not attached to the sheet 300, but to itself.

Figure 12A:
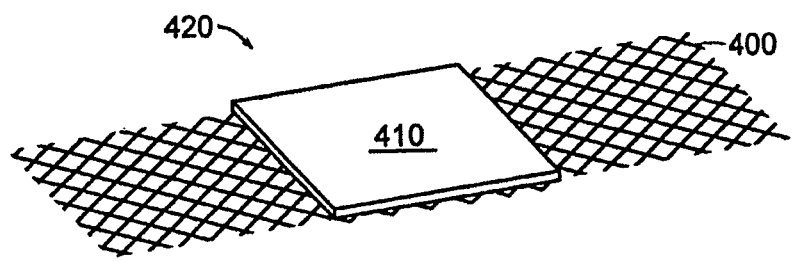
FIG. 12A illustrates a partial perspective view of an alternative embodiment of a sling in accordance with the invention, where the non-synthetic material is attached to the surface of only one side of a portion of the synthetic mesh material.
Figure 12B:
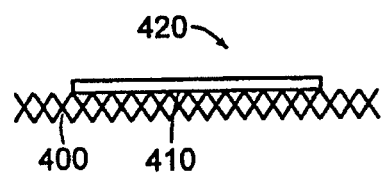
FIG. 12B illustrates a side view of the sling of FIG. 12A.

FIGS. 12A and 12B depict an alternative embodiment of a sling 420 in accordance with the invention. In FIG. 12A, a non-synthetic material 410 is connected to one side of a portion of a mesh sheet 400. FIG. 12B shows a side view of a portion of the sling 420 from FIG. 12A. The non-synthetic material 410 can be attached to the sheet 400 by, e.g., glue, sutures, staples, clips, etc. The sheet 400 extends the entire length of the sling 420.

Figure 13A:
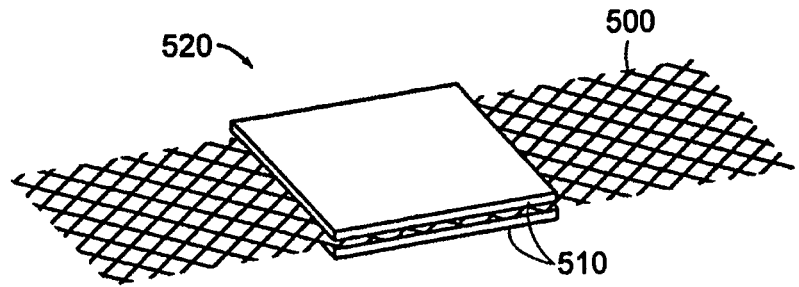
FIG. 13A illustrates a partial perspective view of an alternative embodiment of a sling in accordance with the invention, where the non-synthetic material is attached to the surface of both sides of a portion of the synthetic mesh material.
Figure 13B:
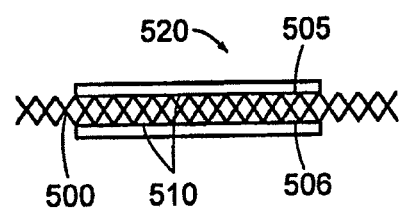
FIG. 13B illustrates a side view of the sling of FIG. 13A.

FIGS. 13A and 13B illustrate an alternative embodiment of a sling 520, wherein two separate pieces of non-synthetic material 510 are attached to both a top surface 505 and a bottom surface 506 of a portion of a mesh sheet 500.

Figure 14:
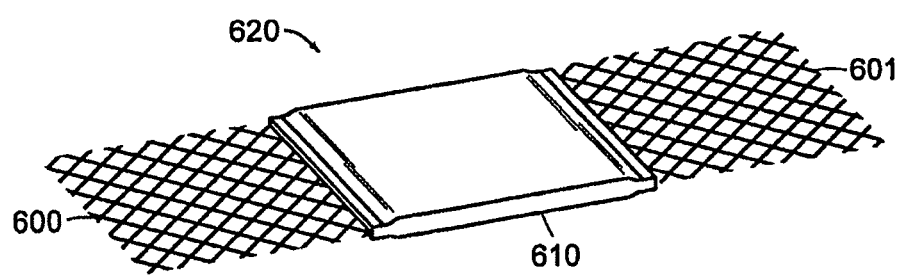
FIG. 14 illustrates a partial perspective view of an alternative embodiment of a sling in accordance with the invention, where both ends of the non-synthetic material are glued to an end of each of two separate pieces of synthetic mesh material.

FIG. 14 depicts yet another embodiment of a sling 620 in accordance with the invention. In FIG. 14, two separate pieces of mesh sheets 600, 601 are glued to opposite ends of a non-synthetic material 610.

Figure 15:
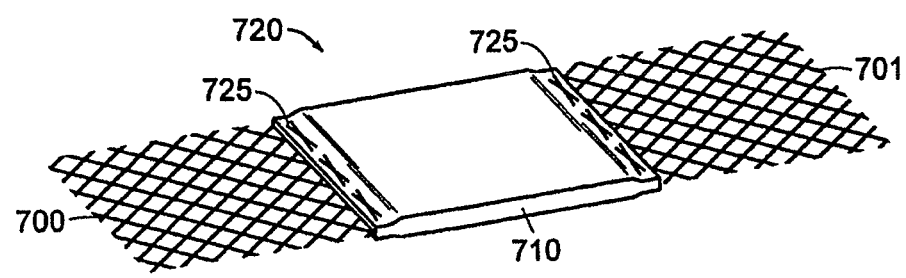
FIG. 15 illustrates a partial perspective view of an alternative embodiment of a sling in accordance with the invention, where both ends of the non-synthetic material are sutured to an end of each of two separate pieces of synthetic mesh material.
Figure 16:
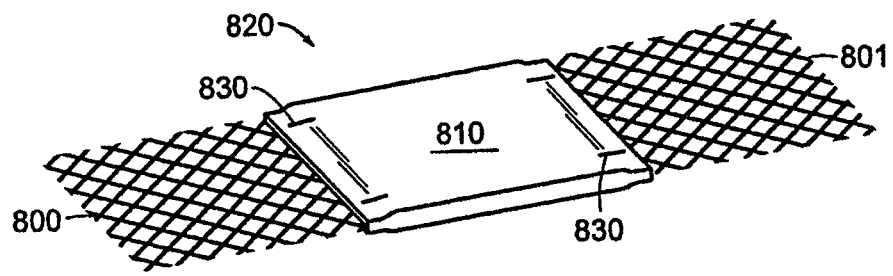
FIG. 16 illustrates a partial perspective view of an alternative embodiment of a sling in accordance with the invention, where both ends of the non-synthetic material are stapled to an end of each of two separate pieces of synthetic mesh material.
Figure 17:
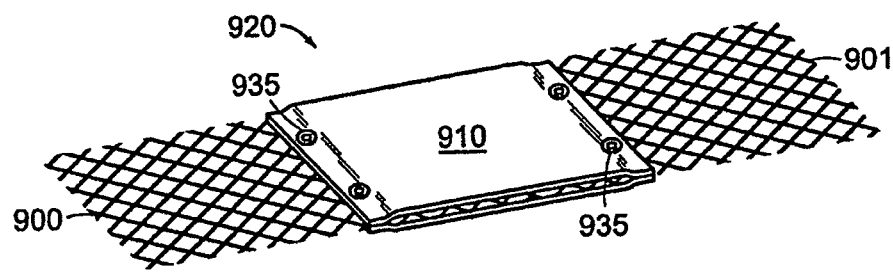
FIG. 17 illustrates a partial perspective view of an alternative embodiment of a sling in accordance with the invention, where both ends of the non-synthetic material are attached via an eyelet rivet to an end of each of two separate pieces of synthetic mesh material.
Figure 18:
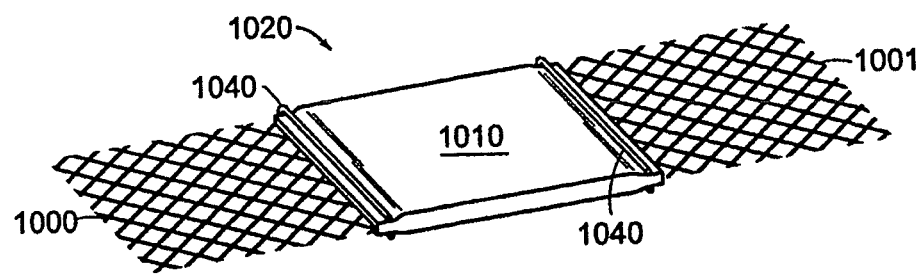
FIG. 18 illustrates a partial perspective view of an alternative embodiment of a sling in accordance with the invention, where both ends of the non-synthetic material are attached via clips to an end of each of two separate pieces of synthetic mesh.

FIGS. 15-18 are structurally similar to the sling 620 of FIG. 14. In FIG. 15, a non-synthetic material 710 is attached to mesh sheets 700, 701 by sutures 725. In FIG. 16, a non-synthetic material 810 is attached to mesh sheets 800, 801 by staples 830. In FIG. 17, a non-synthetic material 910 is attached to mesh sheets 900, 901 by rivets 935. In FIG. 18, a non-synthetic material 1010 is attached to mesh sheets 1000, 1001 by clips 1040.

Figure 19A:
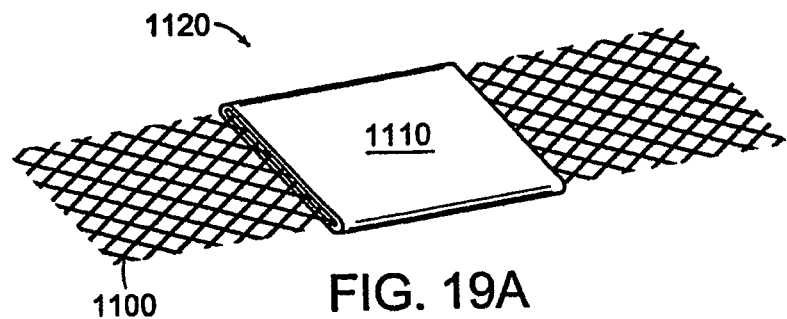
FIG. 19A illustrates a partial perspective view of an alternative embodiment of a sling in accordance with the invention, where the non-synthetic material wraps completely around a portion of the mesh.
Figure 19B:
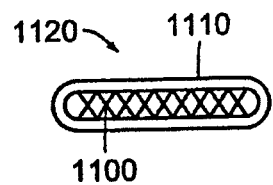
FIG. 19B illustrates a side view of the sling of FIG. 19A.

FIGS. 19A and 19B depict yet another embodiment of a sling 1120 in accordance with the invention. In FIGS. 19A and 19B, a non-synthetic material 1110 wraps around a portion of a mesh sheet 1100 so as to enclose the width-wise ends of a portion of the sheet 1100. In this embodiment, the sheet 1100 extends an entire length of the sling 1120 and the non-synthetic material 1110 is free floating about the sheet 1100. Alternatively, the non-synthetic material 1110 can be secured to the sheet 1100 by any of the methods disclosed herein.

Figure 20:
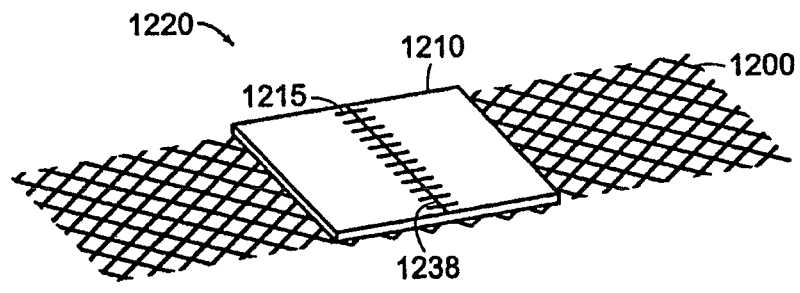
FIG. 20 illustrates a plan view of an alternative embodiment of a sling in accordance with the invention, where the non-synthetic material includes slits.

FIG. 20 depicts another embodiment of a sling 1220 in accordance with the invention. In FIG. 20, a non-synthetic material 1210 is disposed adjacent to a mesh sheet 1200. Slits 1215 are disposed along a second axis 1238 of the non-synthetic material 1210.

In various embodiments, the sling may be pre-soaked in a prescribed drug prior to implantation in a patient's body. Exemplary drugs include neomycin, antimicrobials, and antibiotics, generally. In some embodiments, the hydrophilic material, the drug, or both, when used in combination, release the drug to the patient tissues upon contact. Thus, the drugs that are delivered to the patient tissue surfaces when accessing and inserting the sling are active upon contact with the patient's tissue during implantation of the surgical device.

Similarly, a hydrophobic coating may be employed on one or more surfaces of the sling. Suitable hydrophobic coatings include, but are not limited to, polytetrafluoroethylene, silicon, and Pyrelene. Such hydrophobic coatings may be used in conjunction with and absorb hydrophobic drugs. Suitable hydrophobic drugs include, but are not limited to, ibuprofen, ketoprofen, diclofenac, and lidocaine in hydrophilic form. Where the bonding between these coatings and drugs is weak, the drug that is absorbed will readily release to be delivered to the surfaces it contacts. Alternatively, a stronger bonding affinity may provide a slower timed release of the drug.

The slings disclosed herein are designed to be secured to any suitable support structure of a patient's body. Examples of such structures include but are not limited to the bones, ligaments, fascia, and appropriate muscle structures proximate to the site of attachment. For example, sutures may be used to attach the sling to the Cooper's ligament or the rectus fascia without using a bone anchor. Alternatively, the slings disclosed herein may be secured in an anchorless manner, by any one or more of the approaches described above, in which the structure of the sling (i.e., tanged portions) provides resistance against movement of the sling in the tissue while tissue in growth occurs.

Having thus described certain embodiments of the present invention, various alterations, modifications, and improvements will be apparent to those of ordinary skill. Such alterations, modifications, and improvements are within the spirit and scope of the invention, and the foregoing description of certain embodiments is not exhaustive or limiting.

What is claimed is:

1. A sling for use in a medical application, the sling comprising:
   a first elongated end portion;
   a second elongated end portion; and
   a central portion, wherein the first and second elongated end portions extend from the central portion along a longitudinal axis and a width of the central portion is greater than a width of either the first or second elongated end portions;
   at least one aperture or cut through the sling; and
   a visual guide for aligning the at least one aperture or cut with a urethra of a patient.

2. The sling of claim 1, wherein the at least one aperture or cut is disposed about an axis perpendicular to the longitudinal axis of the sling.

3. The sling of claim 2, wherein the at least one aperture or cut is alternately offset on either side of the axis perpendicular to the longitudinal axis of the sling.

4. The sling of claim 1, wherein the at least one aperture or cut is disposed at a midpoint of the longitudinal axis of the sling.

5. A surgical procedure to treat urinary incontinence, the surgical procedure comprising:
   (a) providing a sling for use in a medical application comprising:
      a first elongated end portion;
      a second elongated end portion; and
      a central portion, wherein the first and second elongated end portions extend from the central portion along a longitudinal axis and a width of the central portion is greater than a width of either the first or second elongated end portions;
      at least one aperture or cut through the sling and
      a visual guide for aligning the at least one aperture with a urethra of a patient; and
   (b) implanting the sling so that the at least one aperture is aligned with the urethra of the patient.

6. The surgical procedure of claim 5, wherein the at least one aperture or cut is disposed about an axis perpendicular to the longitudinal axis of the sling.

7. The surgical procedure of claim 5, wherein the sling include a plurality of apertures or cuts alternately offset on either side of an axis perpendicular to the longitudinal axis of the sling.

8. The surgical procedure of claim 5, wherein the sling is implanted such that at least one aperture or cut is positioned beneath the urethra, wherein the at least one aperture is open when the sling is implanted.

9. The surgical procedure of claim 5, wherein at least one aperture or cut opens when the sling is bent.

10. The surgical procedure of claim 5, wherein the at least one aperture or cut is open when tension is applied about the longitudinal axis of the sling, and at least one aperture or cut is open when the sling is implanted.

11. A sling for use in a medical application, the sling comprising:
- a first elongated end portion;
- a second elongated end portion; and
- a central portion, the first elongated end portion and the second elongated end portion extending away from the central portion, the first elongated end portion, the second elongated end portion and the central portion being arranged along an axis;
- a visual guide disposed on the central portion; and
- at least one aperture or cut through the central portion of the sling, the at least one aperture or cut being in contact with the visual guide.

12. The sling of claim 11, wherein the at least one aperture or cut includes a plurality of apertures arranged along the visual guide, the plurality of apertures being alternatively disposed on a first side of the visual guide and a second side of the visual guide.

13. The sling of claim 12, wherein the apertures of the plurality of apertures are equally spaced along the visual guide.

14. The sling of claim 12, wherein the apertures of the plurality of apertures remain open when a tensioning force is applied to the sling along the axis.

15. The sling of claim 11, wherein the at least one aperture or cut includes a plurality of cuts that are perpendicular to the visual guide.

16. The sling of claim 15, wherein a cut of the plurality of cuts has a first portion disposed on a first side of the visual guide and a second portion disposed on a second side of the visual guide.

17. The sling of claim 15, wherein each cut of the plurality of cuts has a same length, the cuts of the plurality of cuts being vertically aligned.

18. The sling of claim 15, wherein the cuts of the plurality of cuts are alternatively offset with respect to the visual guide.

19. The sling of claim 15, wherein the cuts of the plurality of cuts are equally spaced along the visual guide.

* * * * *